(12) United States Patent
Schipper et al.

(10) Patent No.: US 8,489,181 B1
(45) Date of Patent: Jul. 16, 2013

(54) HEART ELECTRICAL ACTIONS AS BIOMETRIC INDICIA

(75) Inventors: John F. Schipper, Palo Alto, CA (US); Sorin V. Dusan, Sunnyvale, CA (US); Charles C. Jorgensen, Palo Alto, CA (US); Eugene Belousof, Alexandria, VA (US)

(73) Assignee: The United States of America as Represented by the Administrator of the National Aeronautics & Space Administration (NASA), Washington, DC (US)

( * ) Notice: Subject to any disclaimer, the term of this patent is extended or adjusted under 35 U.S.C. 154(b) by 1213 days.

(21) Appl. No.: 12/319,220

(22) Filed: Jan. 2, 2009

(51) Int. Cl.
*A61B 5/04* (2006.01)

(52) U.S. Cl.
USPC .......................................... 600/509

(58) Field of Classification Search
USPC ................................................. 600/204, 509
See application file for complete search history.

(56) References Cited

U.S. PATENT DOCUMENTS

| | | | |
|---|---|---|---|
| 6,483,929 B1 | 11/2002 | Murakami et al. |
| 6,961,448 B2 | 11/2005 | Nichols et al. |
| 7,171,680 B2 | 1/2007 | Lange |
| 2010/0311482 A1 | 12/2010 | Lange |

*Primary Examiner* — Christopher D Koharski
*Assistant Examiner* — Nadia Ahmad
(74) *Attorney, Agent, or Firm* — John F. Schipper; Robert M. Padilla

(57) ABSTRACT

A method and associated system for use of statistical parameters based on peak amplitudes and/or time interval lengths and/or depolarization-repolarization vector angles and/or depolarization-repolarization vector lengths for PQRST electrical signals associated with heart waves, to identify a person. The statistical parameters, estimated to be at least 192, serve as biometric indicia, to authenticate, or to decline to authenticate, an asserted identity of a candidate person.

9 Claims, 12 Drawing Sheets

HEART ELECTRICAL ACTIONS AS BIOMETRIC INDICIA

ORIGIN OF THE INVENTION

This invention was made, in part, by one or more employees of the U.S. government and may be made, used and/or sold by the U.S. government without payment of royalties or other compensation thereon.

FIELD OF THE INVENTION

This invention relates to use of a physiological parameter as a biometric indicium for authentication of identity of a person.

BACKGROUND OF THE INVENTION

One or more biometric indicia, such as fingerprints, voiceprints, retinal scans and facial features, are often proposed to be used to identify, or to authenticate the asserted identity of, a user who seeks access to a given resource. Approximately a dozen different biometric indicia have been proposed, but implementation methods for some of these approaches have not been disclosed. Many of these biometric indicia are associated with inherent physiological characteristics of the user's body. Another set of such indicia relate to what may be characterized as neuro-physiological ("N-P") characteristics that partly reflect a learning or behavioral process and do not rely exclusively on purely physiological features. Use of one or more of these N-P characteristics as a biometric indicium has received relatively little attention, in part because of the perceived difficulty of implementing a procedure to measure such a characteristic. An example is a sequence of bioelectric signals associated with cycles of the heart.

Cardiac muscle is myogenic and is capable of generating an action potential and depolarizing and repolarizing signals from within the muscle itself. An intrinsic conduction system (ICS), a group of specialized cardiac cells, passes an electrical signal throughout the heart. The ICS includes a sino-atrial (SA) node, an atrio-ventrical (AV) node, the bundle of His, right and left bundle branches, and the Purkinje fibers, as illustrated in FIG. 1. These components spread the depolarization waves from the top (atria) of the heart down through the ventricles. The autonomic nervous system modulates the rhythm, rate and strength of cardiac contraction. When the cardiac muscle fibers contract, the volumes within the two atrial or two ventricle chambers are reduced and blood pressure increases. The (smaller) atrial chambers receive blood from the veins and pump the blood into the (larger) ventricle chambers, which pump blood out into the major arteries. The heart cycle normally begins in the right atrial chamber, and spreads to the left atrial chamber and to the two ventricles. The atrial contraction is followed by the ventricular contraction in each cycle.

Simultaneous contraction of the large number of fibers in the ICS generates an electrical field that can be measured at the body surface using an electrocardiograph (ECG). This electrical signal includes a sequence of PQRST complexes, one of which is schematically illustrated in FIG. 2. The time interval between two consecutive R signal peaks, referred to as an R-R interval, corresponds to a heart pulse, with a rate that normally lies in a range of 60-90 beats per minute (bpm). The P signal corresponds to atrial depolarization (right side, followed by left side); the larger QRS complex corresponds to depolarization of the ventricles and (smaller magnitude) repolarization of the atria; and the T signal corresponds to repolarization of the ventricles. A weaker U signal occasionally appears on the chart, representing remnants of ventricular repolarization, but is not shown in FIG. 2.

According to naming conventions accepted by most cardiology workers, a time increment with a straight line amplitude extending between two consecutive signals, for example, from the end of a P wave to the beginning of an immediately following Q wave, is referred to as a "segment;" and a time increment that includes at least one wave, with a graph that is at least partly curved, for example, from the beginning of a Q wave to the beginning of an S wave, is referred to as an "interval." Herein, a "wave," such as a P wave, will refer to the curvilinear graph (only) portion of a time interval, not including the associated time segment. Examples of a "wave", of a "segment," and of an "interval" are illustrated in FIGS. 3A-3B, 3C and 3D-3G, respectively.

Standard electrocardiography involves multiple recordings of a PQRST complex, referred to as "leads," which are obtained from a plurality o felectrodes or electrode pairs, placed at spaced apart locations on a patient's body. Unipolar and bipolar leads are frequently used in standard electrocardiography, for the following purposes: (i) standard bipolar limb leads (I, II, III); (ii) augmented unipolar limb leads (aVR, aVL, aVF); and (iii) unipolar chest leads (V1, V2, V3, V4, V5 V6). As illustrated in FIG. 4, the corresponding electrode polarities and locations are set forth in Table I. By convention, the right leg is treated as "ground."

TABLE I

Lead Polarities and Locations.

| Lead | Negative Electrode Voltage | Positive Electrode Voltage |
|---|---|---|
| I | right arm | left arm |
| II | right arm | left leg |
| III | left arm | left leg |
| aVR | (left arm + left leg)/2 | right arm |
| aVL | (right arm + left leg)/2 | left arm |
| aVF | (right arm + left arm)/2 | left leg |

The bipolar lead voltages are recorded with reference to a "ground" electrode located on the right leg. The standard limb leads are configured as an equilateral triangle, referred to as Einthoven's triangle, where the following constraint is imposed: sum of the voltages impressed for the lead pairs I and III is equal to the voltage impressed for the lead pair II. As an example, if the QRS impressed voltages for lead pairs I and III are 0.8 mV and −0.3 mV, the QRS impressed voltage for lead pair II is the algebraic sum, 0.5 mV.

The augmented unipolar lead voltages are recorded between a positive electrode, located on one limb (right arm, left arm or left leg), and two negative electrodes, connected together and located on the other two limbs (left arm/left leg, right arm/left leg and right arm/left arm), respectively.

The chest lead voltages are recorded between a positive electrode located on the patient's chest and a negative electrode represented as a sum of voltages for the three standard limb electrodes (right arm, left arm, left leg). A sum of the three standard limb electrode voltages provides a reference value, sometimes referred to as an "indifferent voltage." The locations for the six chest leads are well established in the medical field.

FIG. 4 illustrates placement of some of the electrodes used to measure signals and time intervals that are part of an ECG, indicating placement of standard limb electrodes on the right arm RA, on the left arm LA and on the left leg LL. FIG. 5 illustrates use of an Einthoven triangle to estimate an atrial depolarization angle θ(ad;depol) associated with a P wave. One begins with an equilateral triangle EQTR, with right arm (RA), left arm (LA) and left leg (LL) voltages assigned to the three vertices as shown. An augmented voltage aVF is measured, directed perpendicular to a line segment connecting the vertices RA and LA; the vector length of aVF is a deviation of the RA measured voltage from the (expected) median value, (V(RA)+V(LA)/2, described as aVF=V(LL)−{V(RA)+V(LA)}/2

A second augmented voltage aVL is measured perpendicular to a line segment connecting the vertices RA and LL, with a length represented by a deviation of the measured LA voltage from the expected median value, (V(RA)+V(LL)/2), described as aVL=V(LA)−{V(RA)+V(LL)}/2. The atrial depolarization vector V(ad;depol) is the vector sum of the aVF vector and the aVL vector and is shown in FIG. 5 relative to a centroid CT of the triangle EQTR.

A P-Q time interval, normally of length Δt(p-q)≈120-200 msec, represents conduction time from initiation of atrial depolarization until initiation of ventricular depolarization, which is conventionally measured from the start of the P wave to the start of the Q swave.

Where the ICS is diseased or is affected by presence of Digitalis, the P-Q time interval may lengthen as the pulse rate decreases; a prolonged P-Q interval, substantially beyond 200 msec in length, is often evidence of atrio-ventricular block. An abnormally short P-Q interval, substantially below 120 msec in length, is often associated with hypertension and/or with paroxysms of tachycardia. The P-Q interval can also be shortened where the impulse originates in the AV node, or other atrial locations, rather than in the SA node.

The QRS time interval, normally of temporal length Δt(q-t)≈50-100 msec, represents conduction time from initiation of ventricular depolarization until initiation of ventricular repolarization, and includes spread of the electrical impulse through the ventricular muscle. The P signal is normally gently rounded, not pointed or notched, and has a temporal length ≈50-110 msec. One or more of the P, Q, R, S and/or T peaks may be inverted in FIG. 2, depending upon electrode placement. A QRS interval greater than about 120 msec in temporal length often indicates ventricular arrhythmia or a block of one of the bundles.

Normally, an S-T segment amplitude is approximately equal to a T-P segment amplitude. The amplitude of the S-T segment, relative to the baseline (e.g., elevated or depressed), and the shape of the T signal are often of interest. The T signal is normally rounded and slightly asymmetrical. Presence of a sharply pointed or grossly notched T signal may indicate presence of myocardial infarction (pointed segment) or of pericarditis (notched segment).

In some subjects, a beat (a single PQRST complex) is sometimes missed, as illustrated in FIG. 6. This arises from the particular physiology of that subject and has not (yet) been shown to arise unambiguously from the presence of high stress in that subject.

In normal ECG practice, ten or more electrodes including a ground electrode, are attached to the subject at selected, spaced apart locations. A chart of each PQRST complex is printed separately on a 1 mm×1 mm grid, with 1 mm (horizontal) representing 40 msec (0.04 sec time increment) and 1 mm (vertical) representing 0.1 milliVolts (mV amplitude). An upper limit on amplitude is usually 20-30 mm (2-3 mV). The chart is normally recorded at a velocity of 25 mm/sec or, alternatively, at 50 mm/sec. Measurement of an amplitude of 5 mm (0.5 mV) or less for all components in a PQRST complex is often seen in coronary disease, cardiac failure, emphysema and/or obesity. A T signal with unusually large peak amplitude (above 1 mV) may indicate presence of ischemia without infarction, or hyperkalemia, or psychosis.

ECG analysis is generally limited to medical diagnostics and to comparison of shifts with the passage of time of ECG parameters of interest. No substantial work has been done applying the ECG results to other areas of interest, such as authentication of an asserted identity of a candidate person, through analysis of selected ECG results to provide one or more physiologically based biometric indicia associated with the candidate person. Nor has any substantial use been made of evidence of a malady such as myocardial infarction or pericarditis as a characteristic for verifying the identity of a candidate person.

What is needed is a method and associated system for measuring one or more (preferably several) statistical parameters associated with PQRST complexes for a candidate person and authenticating, or declining to authenticate, the person's asserted identity with a reference person, using a comparison of the measured statistical parameter values (biometric indicia) with corresponding reference parameter values. Optionally, the comparisons should be cumulative so that the biometric indicia test can be made progressively more demanding, to minimize likelihood of commission of a type I error (positive result is false) and/or to balance the likelihoods of commission of a type I error and commission of a type II error (negative result is false) in these comparisons. These comparisons should also allow for possible changes with passage of time of PQRST complex characteristics for a candidate person. Preferably, evidence of presence of a malady in a reference person should be available for biometric use in comparison of a candidate person with this reference person.

SUMMARY OF THE INVENTION

These needs are met by the invention, which provides a method and associated system for authenticating, or declining to authenticate, an identity asserted by a candidate person. The PQRST complexes for two different persons are likely sufficiently different that a comparison will allow discrimination between these persons for at least one parameter. Further, if a reference person is known to have a cardiac-related anomaly, absence of this anomaly in the measured PQRST complex of the candidate person strongly indicates that the candidate person is not the reference person, and conversely; presence of this anomaly in the reference person and in the candidate person supports, but does not necessarily require, a conclusion that the candidate person is the reference person.

In a first contribution, a sequence of measured values is provided for at least one peak signal amplitude value, drawn from a set of measured peak signal amplitude values, a=ap, aq, ar, as and at (positive, negative or zero), for a sequence of PQRST heart electrical signal complexes for a candidate person. A selected combination of one or more statistical parameters, drawn from a set of measured parameters, $sp1(a;meas) = \{$normalized mean $m_n(a;meas)=m(a;meas)/(0.1$ mV), normalized standard deviation $sd_n(a;meas)=sd(a;meas)/|m(a;meas)|$, skewness $sk(a;meas)$, kurtosis $ku(a;meas)\}$, is computed, for at least one of the measured peak signal amplitudes, a=ap, aq, ar, as and/or at. A corresponding combination of one or more reference statistical parameters, drawn from a set of known reference parameters, $sp1(a;ref)=\{$normalized mean $m_n(a;ref)$, normalized standard deviation $sd_n(a;ref)$, skewness $sk(a;ref)$ and kurtosis $ku(a;ref)\}$, is provided, for the corresponding reference peak signal amplitude(s), a=ap, aq, ar, as and at, for PQRST complexes associated with a known reference person.

K1 combinations, numbered k1=1, . . . , K1 (K1≧1) of selected non-negative weight values, w1, w2, w3 and w4 (=1−w1−w2−w3) are associated with magnitudes of the respective differences, $m_n(a;meas)-m_n(a;ref)$, $sd_n(a;meas)-sd_n(a;ref)$, sk(a.meas)−sk(a;ref) and ku(a;meas)_−ku(a;ref), where w1, w2, w3 and w4 may depend upon the index k1. A first difference Δ1(k1), dependent upon these differences with their associated weights, is computed and compared with a first selected range R1(k1) of values. When Δ1(k1) lies in the first range R1(k1) of values, this range condition is interpreted as indicating that the candidate person is likely to be the reference person; when Δ1(k1) does not lie in the first range R1(k1), this condition may be interpreted as indicating that the candidate person is not likely to be the reference person.

In a second contribution, the peak signal amplitudes, a=ap, aq, ar, as and at, are replaced by time interval lengths, Δ=Δt (p-q), Δt(q-r), Δt(r-s), Δt(s-t) and Δt(t-p). A selected combination of one or more statistical parameters, drawn from a set of measured parameters, sp2(Δt;meas)={normalized mean $m_n(\Delta t;meas)$=m(a;meas)/(0.04 sec), normalized standard deviation $sd_n(\Delta t;meas)$=sd(Δt;meas)/m(Δt;meas), skewness sk(Δt;meas), kurtosis ku(Δt;meas)}, is computed, for at least one of the measured time intervals Δ=Δt(p-q), Δt(q-r), Δt(r-s), Δt(s-t) and Δt(t-p). The quantity Δt(t-p) is a time increment associated with a refractory period between an end of a ventricular repolarization signal and a beginning of an atrial depolarization signal for the following heart cycle. A corresponding combination of one or more reference statistical parameters, drawn from a set of known reference parameters, sp2(Δt;ref)={normalized mean $m_n(\Delta t;ref)$, normalized standard deviation $sd_n(\Delta t;ref)$, skewness sk(Δt;ref) and kurtosis ku(Δt;ref)}, is provided, for the corresponding reference time intervals Δt=Δt(p-q), Δt(q-r), Δt(r-s), Δt(s-t) and Δt(t-p), for PQRST complexes associated with a known reference person.

K2 combinations, numbered k2=1, . . . , K2 (K2≧1) of selected non-negative weight values, w1', w2', w3' and w4' (=1−w1'−w'2−w3') are associated with magnitudes of the respective differences, $m_n(\Delta t;meas)-m_n(\Delta t;ref)$, $sd_n(\Delta t;meas)-sd_n(\Delta t;ref)$, sk(Δt.meas)−sk(Δt;ref) and ku(Δt;meas)_−ku(Δt;ref), where w1', w2', w3' and w4' may depend upon the index k2. A second difference Δ2(k2), dependent upon these differences with their associated weights, is computed and compared with a second selected range R2(k2) of values. When Δ2(k2) lies in the second range R2(k2) of values, this range condition is interpreted as indicating that the candidate person is likely to be the reference person; when Δ2(k2) does not lie in the second range R2(k2), this condition may be interpreted as indicating that the candidate person is not likely to be the reference person.

In a third contribution, the measured peak signal amplitude values, a=ap, aq, ar, as and at are replaced by depolarization and repolarization angles, θ=θ(mode;ad;depol), θ(mode;vd;depol) and θ(mode;vr;repol) (mode=meas or ref), associated with the angle θ that the respective atrial depolarization vector V(mode;ad;depol) the ventricular depolarization vector V(mode;vd;depol) and the ventricular repolarization vector V(mode;vr;repol) makes with a reference baseplane, such as a locally horizontal plane, for a sequence of PQRST heart electrical signal complexes for a candidate person. A selected combination of one or more statistical parameters, drawn from a set of measured parameters, sp3(θ;meas)={normalized mean $m_n(\theta;meas)$=m(θ;meas)/(1°), normalized standard deviation $sd_n(\theta;meas)$=sd(θ;meas)/|m(θ;meas)|, skewness sk(θ;meas), kurtosis ku(θ;meas)}, is computed, for at least one of the measured angles, θ=θ(meas;ad;depol), θ(meas;vd; depol) and θ(meas;vr;repol). A corresponding combination of one or more reference statistical parameters, drawn from a set of known reference parameters, sp3(θ;ref)={normalized mean $m_n(\theta;ref)$, normalized standard deviation $sd_n(\theta;ref)$, skewness sk(θ;ref) and kurtosis ku(θ;ref)}, is provided, for the corresponding reference angles θ=θ(ref;ad;depol), θ(ref; vd;depol) and θ(ref;vr;repol), for PQRST complexes associated with a known reference person.

K3 combinations, numbered k3=1, . . . , K3 (K3≧1) of selected non-negative weight values, w1'', w'', w3'' and w''4 (=1−w''−w2''−w3'') are associated with magnitudes of the respective differences, $m_n(\theta;meas)-m_n(\theta;ref)$, $sd_n(\theta;meas)-sd_n(\theta;ref)$, sk(θ.meas)−sk(θ;ref) and ku(θ;meas_−ku(θ;ref), where w1'', w2'', w3'' and w4'' may depend upon the index k3. A third difference Δ3(k3), dependent upon these differences with their associated weights, is computed and compared with a third selected range R3(k3) of values. When Δ3(k3) lies in the third range R3(k3) of values, this range condition is interpreted as indicating that the candidate person is likely to be the reference person; when Δ3(k3) does not lie in the first range R3(k3), this condition may be interpreted as indicating that the candidate person is not likely to be the reference person.

Vectors associated with heart depolarization and repolarization waves are largely predictable, with values that are usually close to their mean values.

In a fourth contribution, the measured peak signal amplitude values, a=ap, aq, ar, as and at are replaced by a length L(mode;ad;depol) of the atrial depolarization vector V(mode; ad;depol), a length L(mode;vd;depol) of the ventricular depolarization vector V(mode;vd;depol) and a length L(mode;vr; repol) of the ventricular repolarization vector V(mode;vr; repol) for a sequence of PQRST heart electrical signal complexes for a candidate person. A selected combination of one or more statistical parameters, drawn from a set of measured parameters, sp4(L;meas)={normalized mean $m_n(L; meas)$=m(L;meas)/(L0), normalized standard deviation $sd_n(L;meas)$=sd(L;meas)/|m(L;meas)|, skewness sk(L;meas), kurtosis ku(L;meas)}, is computed, for at least one of the measured lengths, L=L(meas;ad;depol), L(meas;vd;depol) and L(meas;vr;repol). L0 is a reference length of a selected one of the vectors V(ref;ad;depol), V(ref;vd;depol) and V(ref; vr;repol), in appropriate units. A corresponding combination of one or more reference statistical parameters, drawn from a set of known reference parameters, sp4(L;ref)={normalized mean $m_n(L;ref)$, normalized standard deviation $sd_n(L;ref)$, skewness sk(L;ref) and kurtosis ku(L;ref)}, is provided, for the corresponding reference vector lengths L=L(ref;ad;depol), L(ref;vd;depol) and L(ref;vr;repol), for PQRST complexes associated with a known reference person.

K4 combinations, numbered k4=1, . . . , K4 (K4≧1) of selected non-negative weight values, w'''1, w2''', w3''' and w4''' (=1−w1'''−w2'''−w3''') are associated with magnitudes of the respective differences, $m_n(L;meas)-m_n(L;ref)$, $sd_n(L; meas)-sd_n(L;ref)$, sk(L.meas)−sk(L;ref) and ku(L;meas_−ku (L;ref), where w1''', w2''', w3''' and w4''' may depend upon the index k4. A fourth difference Δ4(k4), dependent upon these differences with their associated weights, is computed and compared with a fourth selected range R4(k4) of values. When Δ4(k4) lies in the fourth range R4(k4) of values, this range condition is interpreted as indicating that the candidate person is likely to be the reference person; when Δ1(k4) does not lie in the fourth range R4(k4), this condition may be interpreted as indicating that the candidate person is not likely to be the reference person.

The difference tests for Δ1(k1), Δ2(k2), Δ3(k3) and Δ4(k4) may be performed individually and/or may be combined in pairs and/or combined as a triple test to determine if the candidate person is likely to be, or is not likely to be, the same as the reference person.

The preceding analysis extends to cross-correlation variables <a1·a2>, with a1, a2={ap, aq, ar, as or at} (a1≠a2), to <Δt1·Δt2>, with Δt1, Δt2={Δt(p-q), Δt(q-r), Δt(r-s), Δt(s-t) or Δt(t-p)} (Δt1≠Δt2), to <θ1|θ2> with θ1, θ3={θ(mode;ad; depol), θ(mode;vd;depol) or θ(mode;vr;repol)} (θ1≠θ3), to <L1·L4>, with L1, L4=L(mode;ad;depol), L(mode;vd;depol) and L(mode;vr;repol) (L1≠L4), and to cross-deviation variables <a1·Δt2>, <a1·θ3>, <Δt2·θ3>, <a1·L4>, <Δt2·θ3>, <Δt2·L4> and <θ3·L4>.

Where an ECG of the reference person indicates presence of a non-trivial cardiovascular malady, such as a previous myocardial infarction or pericarditis, presence or absence of this malady in the ECG results of the candidate person can provide support for, or refutation of, congruence of the candidate person and the reference person.

DESCRIPTION OF BEST MODE OF THE INVENTION

Figure 1:
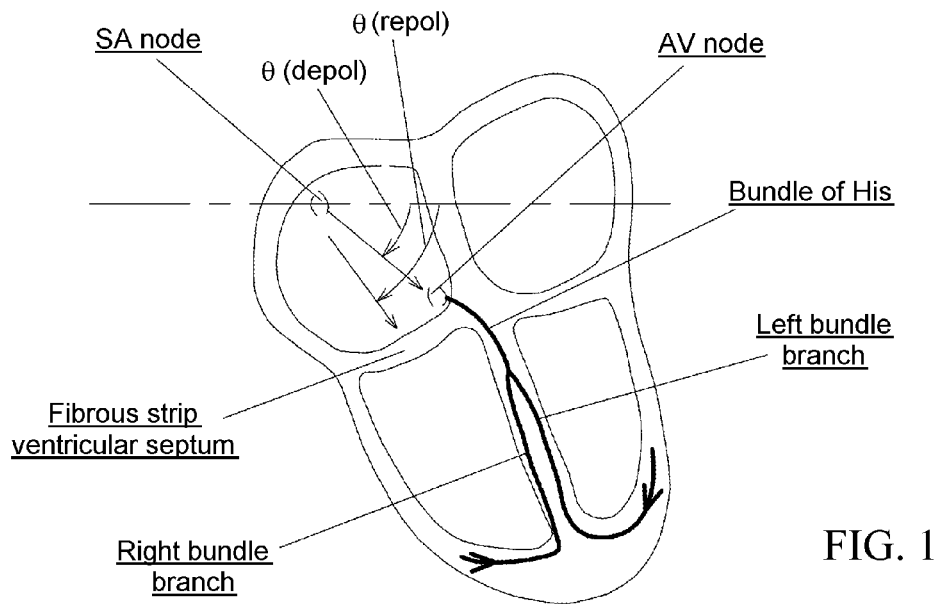
FIG. 1 schematically illustrates a human heart.
Figure 2:
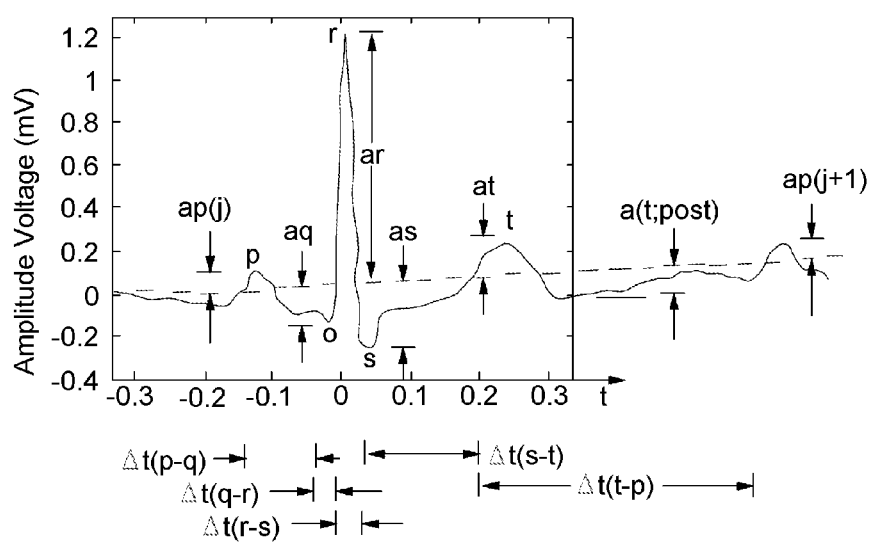
FIG. 2 schematically illustrates a representative PQRST electrical signal complex generated in association with a human heart.
Figure 3D:
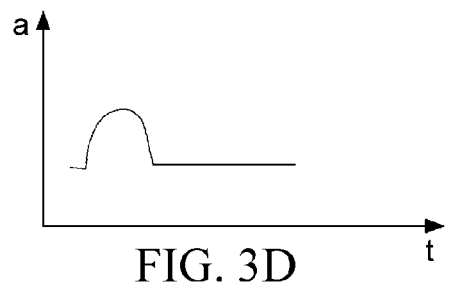
FIGS. 3A-3G illustrate "waves", a "segment" and "intervals."
Figure 3A:
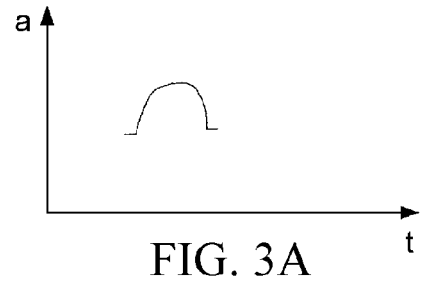
Figure 3E:
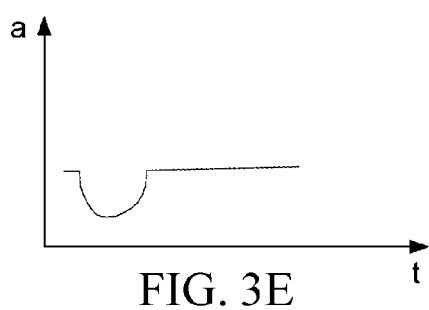
Figure 3B:
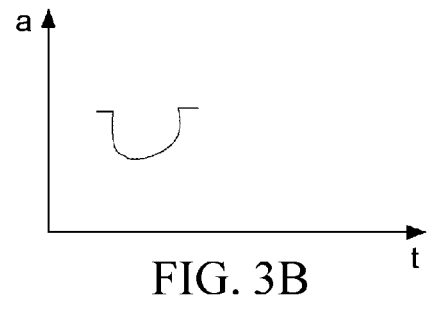
Figure 3F:
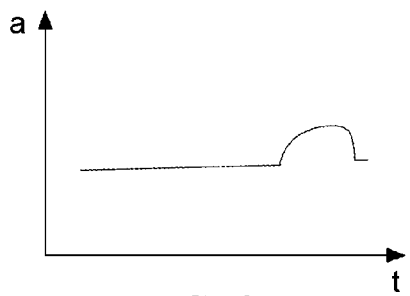
Figure 3C:
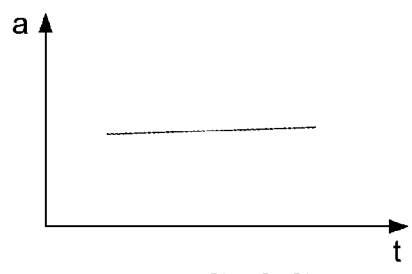
Figure 3G:
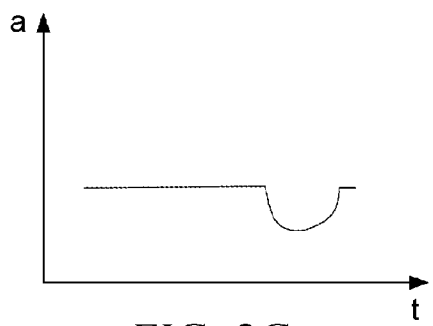
Figure 4:
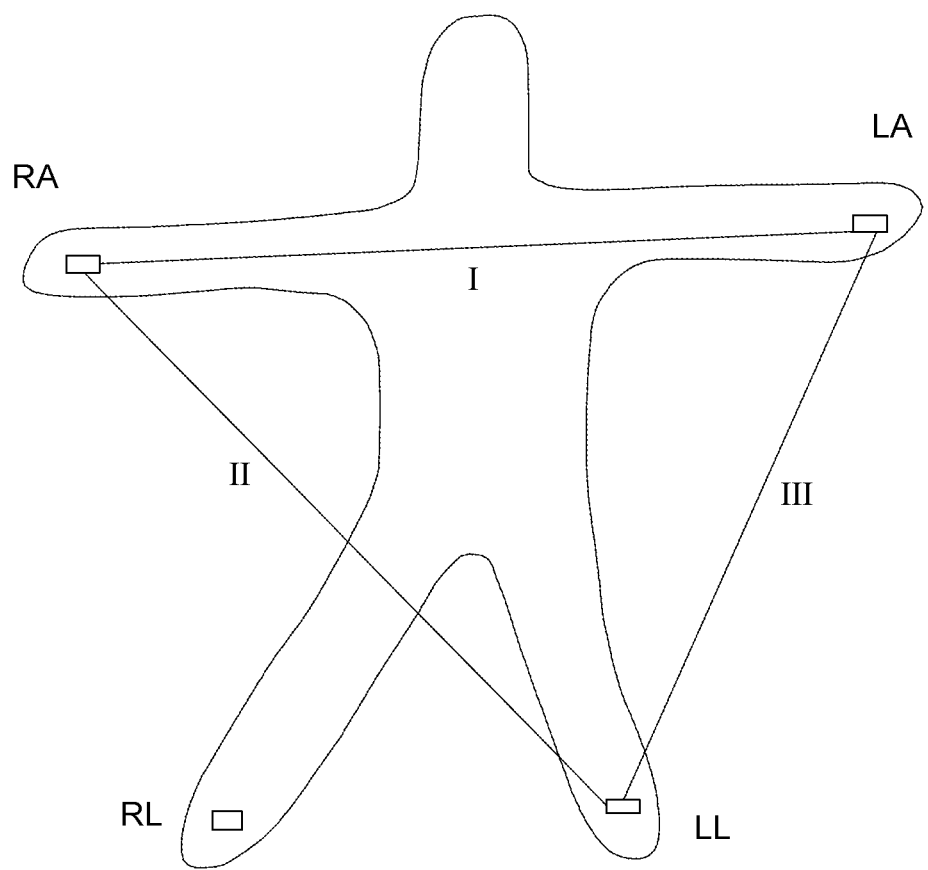
FIG. 4 schematically illustrates electrode placement for an ECG.
Figure 5:
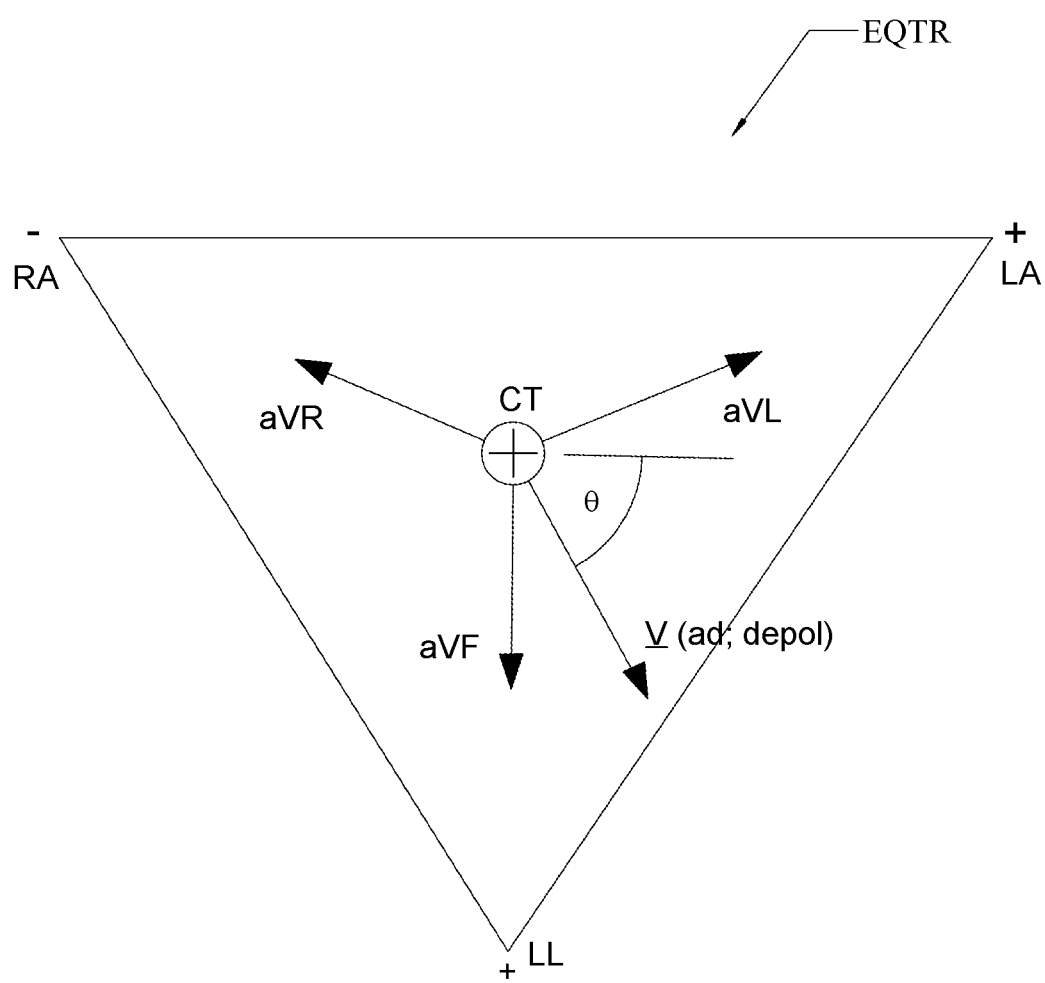
FIG. 5 illustrates use of an Einthoven triangle.

In one graphical presentation, a PQRST electrical signal curve produced in a cycle of the heart, illustrated schematically in FIG. 2, has three maxima and two minima, spaced apart in time from each other and has at least 16 independent associated values: five extremum or peak amplitude values (ap, aq, ar, as, at), plus five signal-to-signal temporal separation values (e.g., Δt(p-q), Δt(q-r), Δt(r-s), Δt(s-t), Δt(t-p)), measured between time points for two consecutive signals (P, Q, R, S, T) of a single PQRST complex or between two consecutive complexes, three depolarization and repolarization angles, θ(ad;depol), θ(vd;depol) and θ(vr;repol), for atrial depolarization (ad) vectors, ventricular depolarization (vd) vectors and ventricular repolarization (vr) vectors measured relative to a selected baseplane, such as a locally horizontal plane or locally vertical plane, plus three vector lengths (magnitudes) L(ad;depol), L(vd;depol) and L(vr;;repol), for the ad, vd and vr vectors. Statistical parameters (normalized mean, normalized standard deviation, skewness, kurtosis) of any subset, or of the full set, of these 16 values can be used to partly or wholly characterize a person. Because an ECG works with as many as 12 signal channels, processed from signals collected at 10 or more spaced apart electrodes located on a person's body, as many as 12≠16=192 parameters are available for statistical comparison of a candidate person and a reference person.

Consider, for example, the variable aq, which is the curve extremum value associated with the q-component of the PQRST complex for a particular channel no. b in FIG. 2 (b=1, . . . , 12), and consider a sequence of measurements of peak values aq(j;b) (j=1, 2, . . . , J; J≧4) of aq for J heart cycles (J≧4), not necessarily consecutive. The normalized mean, normalized standard deviation, skewness and kurtosis for the variable a=ap, aq, ar, as and/or at are defined, respectively, as $$m(a;meas) = \sum_{j=1}^{J} aq;(j;meas)/J, \tag{1}$$

$$m_n(a;meas)=m(a;meas)/(0.1\ mV), \tag{2}$$

$$sd(a;meas)^2 = \sum_{j=1}^{J}(a(j;meas) - m(a;meas))^2 / (J-1), \tag{3}$$

$$sd_n(a;meas)=sd(a;meas)/m(a;meas), \tag{4}$$

$$sk(a;meas) = \sum_{j=1}^{J}(a(j;meas) - m(a;meas))^3 / (J-1)sd(a;meas)^3, \tag{5}$$

$$ku(a;meas) = \sum_{j=1}^{J}(a(j;meas) - m(a;meas))^4 / (J-1)sd(a;meas)^4 - 3, \tag{6}$$

Figure 7A:
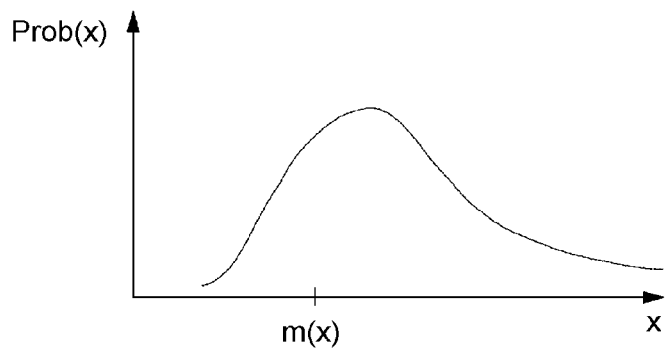
FIGS. 7A and 7B illustrate positive and negative skewness.
Figure 7B:
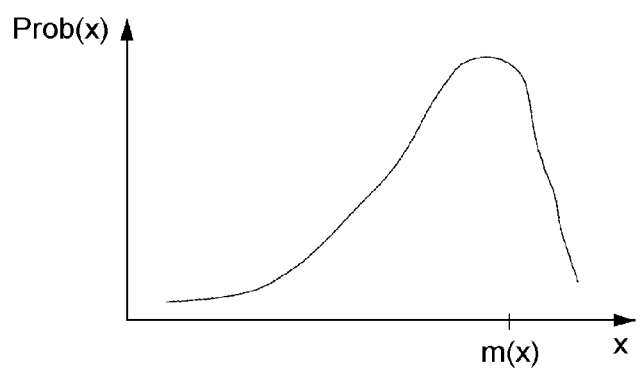
Figure 6:
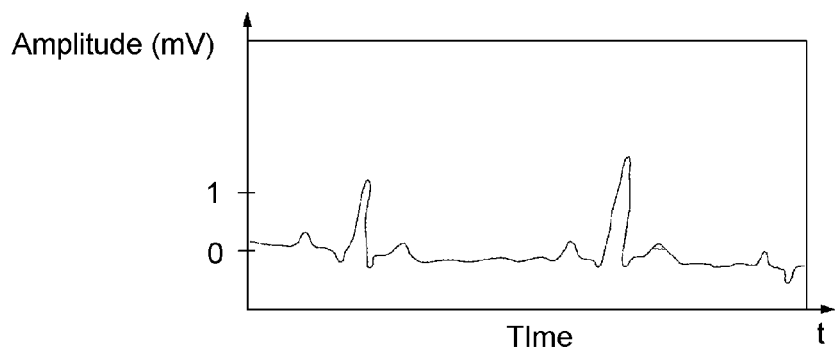
FIG. 6 illustrates a sequence of PQRST complexes, with one missed PQRST complex.

The skewnness coefficient sk(a;meas) is a measure of non-symmetry of the variable a about the mean value m(a;meas). The skewness for a normally distributed variable is 0. A positive value of skewness indicates that the positive branch (a>m(a;meas)) of the statistical distribution has a longer tail than the negative branch (a<m(a;meas)), and inversely for a negative value of skewness, as illustrated in FIGS. 7A and 7B.

The kurtosis coefficient ku(a;meas) is a measure of "sharpness of peak" of the variable a, when compared to a normally distributed variable, which has a kurtosis of 0. A positive (or negative) value of kurtosis indicates that the variable a is more sharply peaked (or less sharply peaked) than a corresponding normally distributed variable.

In a first contribution, a sequence of measured values is provided for at least one peak signal amplitude value, drawn from a set of measured peak signal amplitude values, a=ap, aq, ar, as and at (positive, negative or zero), for a sequence of PQRST heart electrical signal complexes for a candidate person. A selected combination of one or more statistical parameters, drawn from a set of measured parameters, sp1(a;

meas)={normalized mean $m_n$(a;meas)=m(a;meas)/(0.1 mV), normalized standard deviation $sd_n$(a;meas)=sd(a;meas)/|m(a;meas)|, skewness sk(a;meas), kurtosis ku(a;meas)}, is computed, for at least one of the measured peak signal amplitudes, a=ap, aq, ar, as and/or at. A corresponding combination of one or more reference statistical parameters, drawn from a set of known reference parameters, sp1(a;ref)={normalized mean $m_n$(a;ref), normalized standard deviation $sd_n$(a;ref), skewness sk(a;ref) and kurtosis ku(a;ref)}, is provided, for the corresponding reference peak signal amplitude(s), a=ap, aq, ar, as and at, for PQRST complexes associated with a known reference person.

K1 combinations, numbered k1=1, . . . , K1 (K1≧1) of selected non-negative weight values, w1, w2, w3 and w4 (=1−w1−w2−w3) are associated with magnitudes of the respective differences, $m_n$(a;meas)−$m_n$(a;ref), $sd_n$(a;meas)−$sd_n$(a;ref), sk(a.meas)−sk(a;ref) and ku(a;meas_−ku(a;ref), where w1, w2, w3 and w4 may depend upon the index k1. A first difference Δ1(k1), dependent upon these differences with their associated weights, is computed and compared with a first selected range R1(k1) of values. When Δ1(k1) lies in the first range R1(k1) of values, this range condition is interpreted as indicating that the candidate person is likely to be the reference person; when Δ1(k1) does not lie in the first range R1(k1), this condition may be interpreted as indicating that the candidate person is not likely to be the reference person.

The system also measures the variables Δt=Δt(p-q;meas), Δt(q-r;meas), Δt(r-s;meas), Δt(s-t;meas) and/or Δt(t-p;meas), The quantity Δt(t-p) is a time increment associated with a refractory period between an end of a ventricular repolarization signal and a beginning of an atrial depolarization signal for the following heart cycle. The system computes one or more of the corresponding statistical parameters $m_n$(Δt;meas)=m(Δt;meas)/(0.04 sec), $sd_n$(Δt;meas)=sd(Δt;meas)/m(Δt;meas), sk(Δt;meas) and ku(Δt;meas), drawn from a set of statistical parameters sp2(Δt;meas)={$m_n$(Δt;meas), $sd_n$(Δt;meas), sk(Δt;meas), ku(Δt;meas)}, and provides the corresponding statistical parameters $m_n$(Δt;ref)=m(Δt;ref)/(0.04 sec), $sd_n$(Δt;ref)=sd(Δt;ref)/m(Δt;ref), sk(Δt;ref) and ku(Δt;ref), drawn from a set of statistical parameters sp2(Δt;ref)={$m_n$(Δt;ref), $sd_n$(Δt;ref), sk(Δt;ref), ku(Δt;ref)}.

K2 combinations, numbered k2=1, . . . , K2 (K1≧1) of selected non-negative weight values, w1', w2', w3' and w4' (=1−w1'−w'2−w3') are associated with magnitudes of the with the respective differences, $m_n$(Δt;meas)−$m_n$(Δt;ref), $sd_n$(Δt;meas)−$sd_n$(Δt;ref), |sk(Δt.meas)−sk(Δt;ref) and ku(Δt;meas)_−ku(Δt;ref), where w1', w2', w3' and w4' may depend upon the index k2.

A second difference Δ2(k2), dependent upon these differences with their associated weights, is computed and compared with a second selected range R2(k2) of values. When Δ2(k2) lies in the second range R2(k2) of values, this range condition is interpreted as indicating that the candidate person is likely to be the reference person; when Δ2(k2) does not lie in the second range R2(k2), this condition may be interpreted as indicating that the candidate person is not likely to be the reference person.

The system also measures the angle variables θ(mode;ad;depol), θ(mode;vd;depol) and θ(mode;vr;repol), associated with the angle θ that the respective atrial depolarization vector V(mode;ad;depol), the ventricular depolarization vector V(mode;vd;depol) and the ventricular repolarization vector V(mode;vr;repol) makes, respectively, with a reference baseplane, such as a locally horizontal plane. The system computes one or more statistical parameters, drawn from a set of measured parameters, sp3(θ;meas)={normalized mean $m_n$(θ;meas)=m(θ;meas)/(1°), normalized standard deviation $sd_n$(θ;meas)=sd(θ;meas)/|m(θ;meas)θ, skewness sk(θ;meas), kurtosis ku(θ;meas)} and provides corresponding statistical parameters, drawn from a set of reference parameters sp3(θ;ref)={normalized mean $m_n$(θ;ref)=m(θ;ref)/(1°), normalized standard deviation $sd_n$(θ;ref)=sd(θ;ref)/|m(θ;ref)|, skewness sk(θ;ref), kurtosis ku(θ;ref)}.

K3 combinations, numbered k3=1, . . . , K3 (K3≧1) of selected non-negative weight values, w1", w", w3" and w"4 (=1−w"−w2"−w3") are associated with magnitudes of the respective differences, $m_n$(θ;meas)−$m_n$(θ;ref), |$sd_n$(θ;meas)−$sd_n$(θ;ref), sk(θ.meas)−sk(θ;ref)| and ku(θ;meas_−ku(θ;ref), where w1", w2", w3" and w4" may depend upon the index k3.

A third difference Δ3(k3), dependent upon these differences with their associated weights, is computed and compared with a second selected range R3(k3) of values. When Δ3(k3) lies in the third range R3(k3) of values, this range condition is interpreted as indicating that the candidate person is likely to be the reference person; when Δ3(k3) does not lie in the third range R3(k3), this condition may be interpreted as indicating that the candidate person is not likely to be the reference person.

The system also measures the vector length variables L(mode;ad;depol), L(mode;vd;depol) and L(mode;vr;repol), associated with the atrial depolarization vector V(mode;ad;depol), the ventricular depolarization vector V(mode;vd;depol) and the ventricular repolarization vector V(mode;vr;repol) respectively. A selected combination of one or more statistical parameters, drawn from a set of measured parameters, sp4(L;meas)={normalized mean $m_n$(L;meas)=m(L;meas)/(L0), normalized standard deviation $sd_n$(L;meas)=sd(L;meas)/|m(L;meas)|, skewness sk(L;meas), kurtosis ku(L;meas)}, is computed, for at least one of the measured lengths, L=L(meas;ad;depol), L(meas;vd;depol) and L(meas;vr;repol). L0 is a reference length of a selected one of the vectors V(ref;ad;depol), V(ref;vd;depol) and V(ref;vr;repol), in appropriate units. A corresponding combination of one or more reference statistical parameters, drawn from a set of known reference parameters, sp4(L;ref)={normalized mean $m_n$(L;ref), normalized standard deviation $sd_n$(L;ref), skewness sk(L;ref) and kurtosis ku(L;ref)}, is provided, for the corresponding reference lengths L=L(ref;ad;depol), L(ref;vd;depol) and L(ref;vr;repol), for PQRST complexes associated with a known reference person.

K4 combinations, numbered k4=1, . . . , K4 (K4≧1) of selected non-negative weight values, w1''', w''', w3''' and w'''4 (=1−w'''−w2'''−w3''') are associated with magnitudes of the respective differences, $m_t$(L;meas)−$m_n$(L;ref), $sd_n$(L;meas)−$sd_n$(L;ref), sk(L.meas)−sk(L;ref) and ku(L;meas_−ku(L;ref), where w1''', w2''', w3''' and w4''' may depend upon the index k4.

A fourth difference, Δ4(k4), dependent upon magnitudes of one or more of the differences, $m_n$(L;meas)−$m_n$(L;ref), $sd_n$(L;meas)−$sd_n$(L;ref), sk(L;meas)−sk(L;ref), and/or ku(L;meas)−ku(L;ref), is computed and compared with a fourth selected range R4(k4) of values. When Δ4(k4) lies in the fourth range R4(k4) of values, this condition is interpreted as indicating that the candidate person is likely to be the reference person; when Δ4(k4) does not lie in the fourth range R4(k4), this condition may be interpreted as indicating that the candidate person is not likely to be the reference person. The values Δ1(k1), Δ2(k2), Δ3(k3) and/or Δ4(k4), relative to the respective ranges R1(k1), R2(k2), R3(k3) and/or R4(k4), can be displayed, graphically or alphanumerically, or another indication can be displayed indicating that the candidate person is likely to be, or is not likely to be, the reference person.

The functional forms of the first, second, third and fourth differences, $\Delta 1(k1)$, $\Delta 2(k2)$, $\Delta 3(k3)$ and $\Delta 4(k4)$, may be chosen independently of each other, as functions of differences of the corresponding statistical measured and statistical reference values. One general class of difference functions is the Minkowski distance, defined as follows.

$$\Delta 1(k1) = \{w1 |m_n(a;\text{meas}) - m_n(a;\text{ref})|^{f1} + w2 |sd_n(a;\text{meas}) - sd_n(a;\text{ref})|^{f1} + w3 |sk(a;\text{meas}) - sk(a;\text{ref})|^{f1} + w4 |ku(a;\text{meas}) - ku(a;\text{ref})|^{f1}\}^{1/f1}, \quad (7)$$

$$\Delta 2(k2) = \{w1' |m_n(\Delta t;\text{meas}) - m_n(\Delta t;\text{ref})|^{f2} + w2' |sd_n(\Delta t;\text{meas}) - sd_n(\Delta t;\text{ref})|^{f2} + w3' |sk(\Delta t;\text{meas}) - sk(\Delta t;\text{ref})|^{f2} + w4' |ku(\Delta t;\text{meas}) - ku(\Delta t;\text{ref})|^{f2}\}^{1/f2}, \quad (8)$$

$$\Delta 3(k3) = \{w1'' |m_n(\theta;\text{meas}) - m_n(\theta;\text{ref})|^{f3} w2'' |sd_n(\theta;\text{meas}) - sd_n(\theta;\text{ref})|^{f3} + w3'' |sk(\theta;\text{meas}) - sk(\theta;\text{ref})|^{f3} + w4'' |ku(\theta;\text{meas}) - ku(\theta;\text{ref})|^{f3}\}^{1/f3}, \quad (9)$$

$$\Delta 4(k4) = \{w1''' |m_n(L;\text{meas}) - m_n(L;\text{ref})|^{f4} + w2''' |sd_n(L;\text{meas}) - sd_n(L;\text{ref})|^{f4} + w3''' |sk(L;\text{meas}) - sk(L;\text{ref})|^{f4} + w4''' |ku(L;\text{meas}) - ku(L;\text{ref})|^{f4}\}^{1/f4}, \quad (10)$$

where f1, f2, f3 and f4 are independently chosen positive numbers. In Eq. (7) one can prove that, if a particular term, $wm \cdot |f_m(a;\text{meas}) - f_m(a;\text{ref})|$, has wm>0 and the multiplier $|f_m(a;\text{meas}) - f_m(a;\text{ref})|$ is larger than any other multiplier in that sum, the difference $\Delta 1(k1)$ tends to the value $||f_m(a;\text{meas}) - f_m(a;\text{ref})|$ as the power f1 increases without limit (f1→∞). An analogous result is obtained for the difference $\Delta 2(k2)$, for the difference $\Delta 3(k3)$, and for the difference $\Delta 4(k4)$. A choice f1=2 or f2=2 or f3=2 or f4=2 reproduces a weighted Euclidean distance in Eq. (7), Eq. (8), Eq. (9) or Eq. (10). Other functional forms for $\Delta 1(k1)$, $\Delta 2(k2)$, $\Delta 3(k3)$ and $\Delta 4(k4)$ can also be chosen. A choice f1=1 or f2=1 or f3=1 or f4=1 reproduces a weighted quasilinear distance. Use of a maximum likelihood estimator to estimate a log-likelihood statistical distance for verification is discussed in an Appendix.

Where two or more peak signal amplitudes, for example, a=ap and a=ar, are separately examined, the differences $\Delta 1(k1)$ are computed separately for each signal amplitude (ap and ar), using a selected functional form for these differences. For the five-fold set of peak signal amplitudes (ap and/or aq and/or ar and/or as and/or at), the number of different combinations available is $2^5 - 1 = 31$.

Where two or more time intervals, for example, $\Delta t = \Delta t(q-r)$ and $\Delta t = \Delta t(t-p)$, are separately examined, the differences $\Delta 2(k2)$ are computed separately for each signal amplitude ($\Delta t(q-r)$ and $\Delta t(t-p)$), using a selected functional form for these differences. For the five-fold set of time intervals ($\Delta t(p-r)$ and/or $\Delta t(q-r)$ and/or $\Delta t(r-s)$ and/or $\Delta t(s-t)$ and/or $\Delta t(t-p)$), the number of different combinations available is also $2^5 - 1 = 31$.

Where two or more depol/repol angles, for example, $\theta = \theta$(mode;ad;depol) and $\theta = \theta$(mode;vr;repol), are separately examined, the differences $\Delta 3(k3)$ are computed separately for each angle, $\theta$(mode;ad;depol) and $\theta$(mode;vr;repol), using a selected functional form for these differences. For the three-fold set of angles ($\theta$(mode;ad;depol) and/or ($\theta$(mode;vd;depol) and/or $\theta$(mode;vr;repol), the number of different combinations available is $2^3 - 1 = 7$. In a similar manner, for the three-fold set of vector lengths L(mode;ad;depol) and/or L(mode;vd;depol) and/or L(mode;vr;repol), the number of available combinations is $2^3 - 1 = 7$.

In a first embodiment, where a first difference $\Delta 1(k1)$ lies within a first selected range R1(k1) of difference values for each of these K1 combinations; or a second difference $\Delta 2(k2)$ lies within a second selected range R2(k2) of difference values for each of these K2 combinations; or a third difference, $\Delta 3(k3)$ lies within a third selected range R3(k3) of difference values for each of these K3 combinations, or a fourth difference, $\Delta 4(k4)$ lies within a fourth selected range R4(k4) of difference values for each of these K4 combinations (referred to as "range conditions"), the candidate person is determined to be likely to be the reference person. Satisfaction of at least one of the first range condition for $\Delta 1(k1)$, the second range condition for $\Delta 2(k2)$, the third range condition for $\Delta 3(k3)$, and the fourth range condition for $\Delta 4(k4)$ is interpreted as indicating that the candidate person and the reference person are the same person. Where $\Delta 1(k1)$ does not lie in the first range R1(k1), $\Delta 2(k2)$ does not lie in the second range R2(k2), $\Delta 3(k3)$ does not lie in the third range R3(k3), and $\Delta 4(k4)$ does not lie in the fourth range R4(k4) this condition may be interpreted as indicating that the candidate person is likely not the reference person.

In a second embodiment, where at least two of the four range conditions on $\Delta 1(k1)$, $\Delta 2(k2)$, $\Delta 3(k3)$ and $\Delta 4(k4)$ are satisfied, these conditions are interpreted as indicating that the candidate person and the reference person are likely the same person. Where no more than one of the four range conditions on $\Delta 1(k1)$, $\Delta 2(k2)$, $\Delta 3(k3)$ and $\Delta 4(k4)$ is satisfied, this may be interpreted as indicating that the candidate person is likely not the reference person.

In a third embodiment, where at least three of the four range conditions on $\Delta 1(k1)$, $\Delta 2(k2)$, $\Delta 3(k3)$ and $\Delta 4(k4)$ are satisfied, these conditions are interpreted as indicating that the candidate person and the reference person are likely the same person. Where no more than two of the four range conditions on $\Delta 1(k1)$, $\Delta 2(k2)$, $\Delta 3(k3)$ and $\Delta 4(k4)$ are satisfied, this may be interpreted as indicating that the candidate person is likely not the reference person.

In a fourth embodiment, where all four of the range conditions on $\Delta 1(k1)$, $\Delta 2(k2)$, $\Delta 3(k3)$ and $\Delta 4(k4)$ are satisfied, these conditions are interpreted as indicating that the candidate person and the reference person are likely the same person. Where no more than three of the four range conditions on $\Delta 1(k1)$, $\Delta 2(k2)$, $\Delta 3(k3)$ and $\Delta 4(k4)$ are satisfied, this may be interpreted as indicating that the candidate person is likely not the reference person.

For a given (known) person, it may be appropriate to provide two or more combinations of references parameters, sp1(a;ref) and/or two or more sets of reference parameters sp2($\Delta t$;ref) and/or two or more sets of reference parameters sp3($\theta$;ref) and/or two or more sets of reference parameters sp4(L;ref), corresponding to different situations in which these parameters were determined, for comparison with corresponding measurements for the candidate person, for at least two reasons. Where two or more sets of reference person parameters are available, the measured parameters for the candidate person are preferably compared with each of the reference person parameter sets to determine if at least one of the reference person parameter sets is in substantial agreement with the measured candidate person set, as reflected in the difference values $\Delta 1(k1)$, $\Delta 2(k2)$, $\Delta 3(k3)$ and/or $\Delta 4(k4)$.

First, presence of the well known "white coat syndrome" in some reference situations but not in others, may cause an end-to-end reference time interval length $\Delta t(p-p)$ to become significantly smaller in one reference situation than in another situation, for a given reference person. This will cause at least one of the reference time interval lengths, $\Delta t(p-q)$, $\Delta t(q-r)$, $\Delta t(r-s)$, $\Delta t(s-t)$ and $\Delta t(t-p)$, to also become smaller, among other changes. Thus, it may be appropriate to compare two or more measured combinations C1(k1)(a;meas) and C2(k2)($\Delta t$;meas), C3(k3)($\theta$;meas) and C4(k4)(L;meas) against each of two or more corresponding reference combinations for different situations for a given candidate person.

Second, the cardio-physiology of the candidate person may change appreciably with time so that comparison of presently measured ECG parameters with corresponding reference parameters, prepared several months or years earlier, may lead to an increased incidence of Type II errors, wherein the system erroneously declines to identify the candidate person with the reference person.

The locations on the body of the ECG electrodes used to measure the ECG plots for the reference parameter values, x(ref) and Δt(ref) and θ(ref), should be noted carefully and preserved with the reference parameter values themselves. The same body locations should be used for measuring the PQRST complex parameters for the candidate person, to minimize dispersion problems, amplitude distortion problems and/or phase distortion problems associated with transmission of electrical signals through portions of, or along surfaces of, the human body.

Cross-correlations of two or more of the peak amplitude signals ap, aq, ar, as and at, and of the time interval lengths Δt(p-q), Δt(q-r), Δt(r-s), Δt(s-t) and Δt(t-p), and of the propagation angles θ(mode;ad;depol), θ(mode;vd;depol) and θ(mode;vr;repol), and of the vector lengths L(mode;ad;depol), L(mode;vd;depol) and L(mode;vr;repol), can also provide reference parameters, against which the corresponding measured parameters of the candidate person can be compared. A first such parameter is the correlation of two distinct peak amplitude signals, $$\langle a1 \cdot a2 \rangle = \Sigma a1(j) \cdot a2(j)/(J-1), \quad j=1 \ldots J \quad (11)$$

$$a1, a2 = ap, aq, ar, as \text{ or } at \ (a1 \neq a2). \quad (12)$$

A second such parameter is the correlation of two distinct time interval lengths, $$\langle \Delta t1 \cdot \Delta t2 \rangle = \Sigma \Delta t1(j) \cdot \Delta t2(j)/(J-1), \quad j=1 \ldots J \quad (13)$$

$$\Delta t1, \Delta t2 = \Delta t(p-q), \Delta t(q-r), \Delta t(r-s), \Delta t(s-t) \text{ or } \Delta t(t-p) \ (\Delta t1 \neq \Delta t2). \quad (14)$$

A third such parameter is the correlation of two of the three propagation angles $$\langle \theta 1 \cdot \theta 3 \rangle = \Sigma \theta 1(j) \cdot \theta 3(j)/(J-1), \quad j=1 \ldots J \quad (15)$$

$$\theta 1, \theta 3 = \theta(\text{mode};a;\text{depol}), \theta(\text{mode};v;\text{depol}), \theta(\text{mode};v;\text{repol}) \ (\theta 1 \neq \theta 3). \quad (16)$$

A fourth such parameter is the correlation of two of the three vector lengths $$\langle L1 \cdot L3 \rangle = \Sigma L1(j) \cdot L3(j)/(J-1), \quad j=1 \ldots J \quad (17)$$

$$L1, L3 = L(\text{mode};ad;\text{depol}), L(\text{mode};vd;\text{depol}), L(\text{mn-ode};vr;\text{repol}) \ (L \neq L3). \quad (18)$$

Any of the set of $(^5_2)=10$ correlation parameters $\langle a1 \cdot a2 \rangle$ and/or any of the set of $(^5_2)=10$ correlation parameters $\langle \Delta t1 \cdot \Delta t2 \rangle$ and/or any of the set of $(^3_2)=3$ correlation parameters $\langle \theta 1 \cdot \theta 3 \rangle$ and/or any of the set of $(^3_2)=3$ correlation parameters $\langle L1 \cdot L4 \rangle$ can be used as a biometric indicium for comparison of a measured value (for a candidate person) against a corresponding reference value. Again, the difference between the measured parameter value and the corresponding reference value should fall into a selected range, if the candidate person is to be identified as the reference person. Further, one or more of the 26 statistical parameters, $m_n(a)$, $sd_n(a)$, $sk(a)$, $ku(a)$, $m_n(\Delta t)$, $sd_n(\Delta t)$, $sk(\Delta t)$, $ku(\Delta t)$, $m_n(\theta)$, $sd_n(\theta)$, $sk(\theta)$, $ku(\theta)$, $m_n(L)$, $sd_n(L)$, $sk(L)$, $ku(L)$, $\langle a1 \cdot a2 \rangle$, $\langle \Delta t1 \cdot \Delta t2 \rangle$, $\langle \theta 1 \cdot \theta 4 \rangle$, $\langle L1 \cdot L2 \rangle$ $\langle a1 \cdot \Delta t2 \rangle$, $\langle a1 \cdot \theta 3 \rangle$, $\langle a1 \cdot L4 \rangle$, $\langle \Delta t2 \cdot \theta 3 \rangle$, $\langle \Delta t2 \cdot L4 \rangle$ and $\langle \theta 3 \cdot L4 \rangle$ can be used for comparison purposes.

Two or more of the peak signal amplitude variables, a=ap, aq, ar, as and at, may be correlated within a single PQRST complex, because of constraints on signal recovery (positive-to-negative or negative-to-positive) or because of correlations between signal distortions introduced by signal transmissions through one or more body organs or tissues. Two or more of the time interval lengths, Δt=Δt(p-q), Δt(q-r), Δt(r-s), Δt(s-t) and Δt(t-p), may be correlated (within a single PQRST complex or between two consecutive PQRST complexes), because of an overall time constraint that is present. Two or more of the propagation angles, θ1=θ(mode;ad;depol), θ2=θ(mode;vd;depol), and θ3=θ(mode;vr;repol), may be correlated because of geometrical or material constraints, associated with signal propagation adjacent to the heart. Two or more of the propagation vector lengths, L1=L(mode;ad;depol), L2=L(mode;vd;depol), and L3=L(mode;vr;repol), may be correlated because of geometrical or material constraints, associated with signal propagation adjacent to the heart.

The quantity $\langle x1 \cdot \Delta t2 \rangle$, with $(x1, \Delta t2) = \{(ap, \Delta t(p-q)), (aq, \Delta t(p-q)), (aq, \Delta t(q-r)), (ar, \Delta t(q-r)), (ar, \Delta t(r-s)), (as, \Delta t(r-s)), (as, \Delta t(s-t)), (at, \Delta t(s-t)), (at, \Delta t(t-p)) \text{ or } (ap, \Delta t(t-p))\}$, may have non-zero cross-deviation, because the magnitude of a peak (e.g., aq) may be influenced by at least one of the adjacent time interval lengths (e.g., Δt(p-q) and Δt(q-r)). Similar non-zero cross-deviations, $\langle a1 \cdot \theta 3 \rangle$, $\langle a1 \cdot L4 \rangle$, $\langle \Delta t2 \cdot \theta 3 \rangle$, $\langle \Delta t2 \cdot L4 \rangle$ and $\langle \theta 3 \cdot L4 \rangle$, may occur because of interactions of the various ECG variables.

One can also use cross-deviations of peak amplitudes, time interval lengths and the propagation angles for comparison purposes, such as the 24 parameters $$\langle a1 \cdot \Delta t2 \rangle = \Sigma_j a1(j) \cdot \Delta t2(j)/(J-1), \quad (19)$$

$$(a1, \Delta t2) = \{ap \cdot \Delta t(p-q), aq \cdot \Delta t(p-q), xq \cdot \Delta t(q-r), ar \cdot \Delta t(q-r), ar \cdot \Delta t(r-s), as \cdot \Delta t(r-s), as \cdot \Delta t(s-t), at \cdot \Delta t(s-t), at \cdot \Delta t(t-p) \text{ or } ap \cdot \Delta t(t-p)\} \quad (20)$$

$$\langle a1 \cdot 3 \rangle = \Sigma_j a1(j) \cdot \theta 3(j)/(J-1), \quad (21)$$

$$(a1, \theta 3) = \{ap \cdot \theta(ad; \text{depol}), aq \cdot \theta(ad; \text{depol}), aq \cdot \theta(vd; \text{depol}), ar \cdot \theta(vd; \text{depol}), as \cdot \theta(vd; \text{depol}), as \cdot \theta(vr; \text{repol}), at \cdot \theta(vr; \text{repol})\}, \quad (22)$$

$$<a1 \cdot L4> = \Sigma_j a1(j) L4(j)/(J-1), \quad (23)$$

$$(a1, L4) = \{ap \cdot L(ad;depol), aq \cdot L(ad;depol), aq \cdot L(vd;depol), ar \cdot L(vd;depol), as \cdot L(vd;depol), as \cdot L(vr;repol), at \cdot L(vr;repol)\}, \quad (24)$$

$$<\Delta t2 \cdot \theta 3> = \Sigma_j \Delta t2(j) \cdot \theta 3(j)/(J-1), \quad (25)$$

$$(\Delta t2, \theta 3) = \{\Delta t(p-q) \cdot \theta(ad;depol), \Delta t(q-r) \cdot \theta(vd;depol), \Delta t(r-s) \cdot \theta(vd;depol), \Delta t(s-t) \cdot \theta(vd;depol), \Delta t(s-t) \cdot \theta(vr;repol), \Delta t(t-p) \cdot \theta(vr;repol), \Delta t(t-p) \cdot \theta(ad;depol)\} \quad (26)$$

$$<\Delta t2 \cdot L4> = \Sigma_j \Delta t2(j) L(j)/(J-1), \quad (27)$$

$$(\Delta t2, L4) = \{\Delta t(p-q) \cdot L(ad;depol), \Delta t(q-r) \cdot L(vd;depol), \Delta t(r-s) \cdot L(vd;depol), \Delta t(s-t) \cdot L(vd;depol), \Delta t(s-t) \cdot L(vr;repol), \Delta t(t-p) \cdot L(vr;repol), \Delta t(t-p) \cdot L(ad;depol)\}, \quad (28)$$

$$<\theta 3 \cdot L4> = \Sigma_j \theta 3(j) L4(j)/(J-1) \quad (29)$$

$$(\theta 3, L4) = \{\theta(ad;depol) \cdot L(ad;depol), \theta(vd;depol) \cdot L(ad;depol), \theta(ad;depol) \cdot L(vd;depol), \theta(vd;depol) \cdot L(vd;depol), \theta(vd;depol) \cdot L(vr;repol), \theta(vr;repol) \cdot L(vd;depol), \theta(vr;repol) \cdot L(vd;repol)\}. \quad (30)$$

One can also use certain related functions of the correlations for comparison purposes. Consider, for example, a cross-correlation function $$\mu 12(\lambda) = \sum_{j=1}^{J} (a1(j) - \lambda \cdot a2(j))^2 / (J-1)$$

$$= <a1^2> - 2\lambda <a1 \cdot x2> + \lambda^2 <a2^2> \quad (31)$$

$$\mu 12(\lambda=1) = <a1^2> - 2<a1 \cdot a2> + <a2^2>. \quad (32)$$

The function $\mu 12(\lambda)$ is minimized by the choice $$\lambda = \lambda(\min) = <a1 \cdot a2>/<a2^2>, \quad (33)$$

$$\mu 12(\lambda = \lambda(\min)) = <a1^2> - \{<a1 \cdot a2>\}^2 / <a2^2>. \quad (34)$$

Another quantity of interest is a cross-standard deviation, defined as $$\mathrm{var}(a1, a2) = \sum_{j=1}^{J} (a1(j) - m(a1)) \cdot (a2(j) - m(a2))/(J-1)$$

$$= <a1 \cdot a2> - m(a1) \cdot m(a2). \quad (35)$$

Similar results are obtained where the variable a is replaced by the variable $\Delta t$ or by the variable $\theta$.

Figure 8:
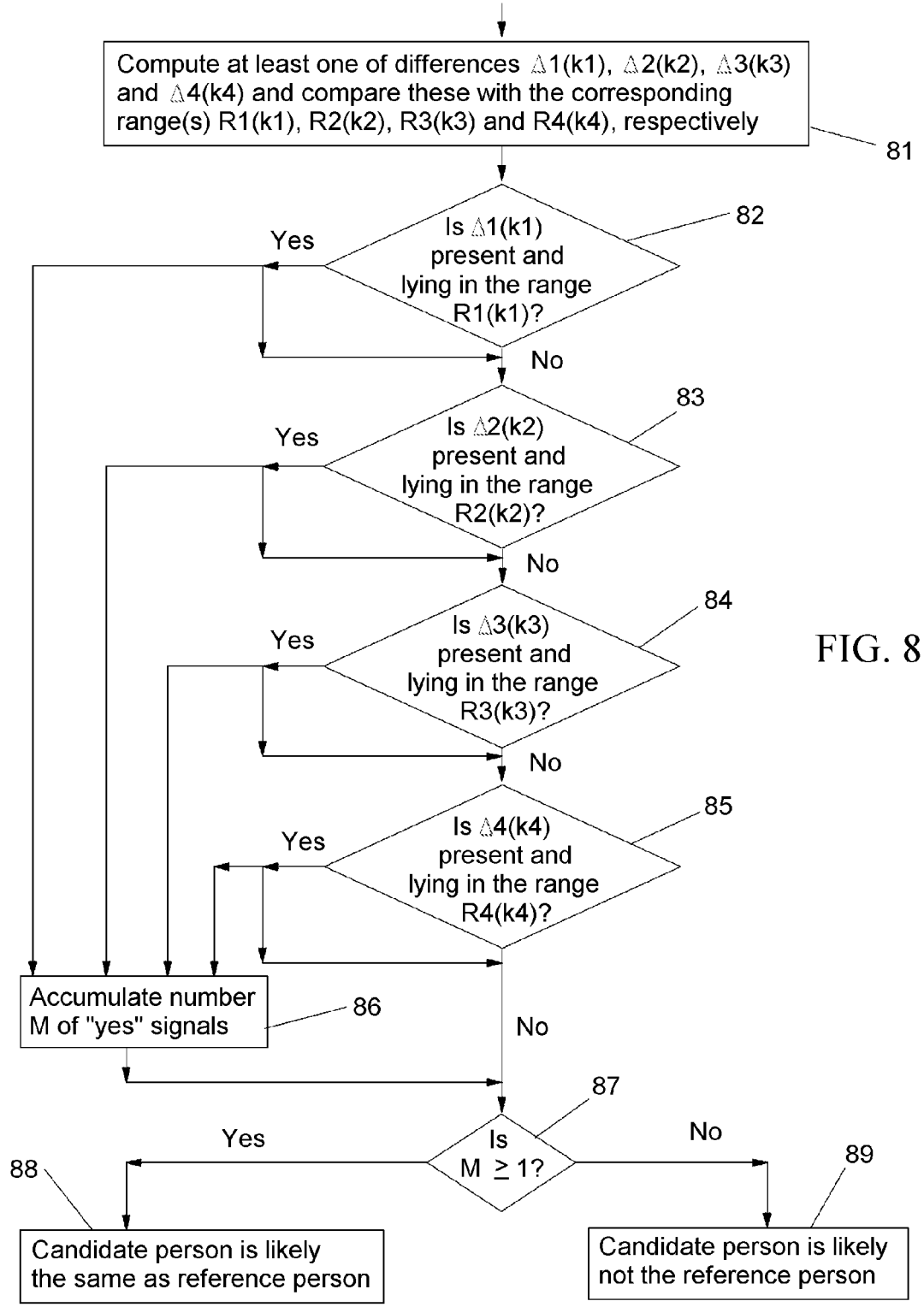
FIGS. 8, 9, 10 and 11 illustrate procedures to practice the invention.

FIG. 8 is a flow chart illustrating a first embodiment of the invention. In step 81, at least one of the difference values, $\Delta 1(k1)$, $\Delta 2(k2)$, $\Delta 3(k3)$ and $\Delta 4(k4)$ is computed and compared with the corresponding range, R1(k1), R2(k2), R3(k3) and R4(k4), respectively. The system determines if $\Delta 1(k1)$ is present (computed) and lies in the first range R1(k1), in step 82; if $\Delta 2(k2)$ is present (computed) and lies in the second range R2(k2), in step 83, if $\Delta 3(k3)$ is present (computed) and lies in the third range R3(k3), in step 84, and/or if $\Delta 4(k4)$ is present (computed) and lies in the fourth range R4(k4), in step 85. The number M of "yes" answers in steps 82-85 is accumulated in step 86. If at least one of the answers to the queries in step 82, 83, 84 and 85 is "yes" ($M \geq 1$ in step 87), the system interprets this condition as indicating that the candidate person is likely the reference person, in step 88. If none of the answers to the queries in step 82, step 83, step 84 and step 85 is "yes," the system optionally interprets this condition as indicating that the candidate person is likely not the reference person, in step 89.

Figure 9:
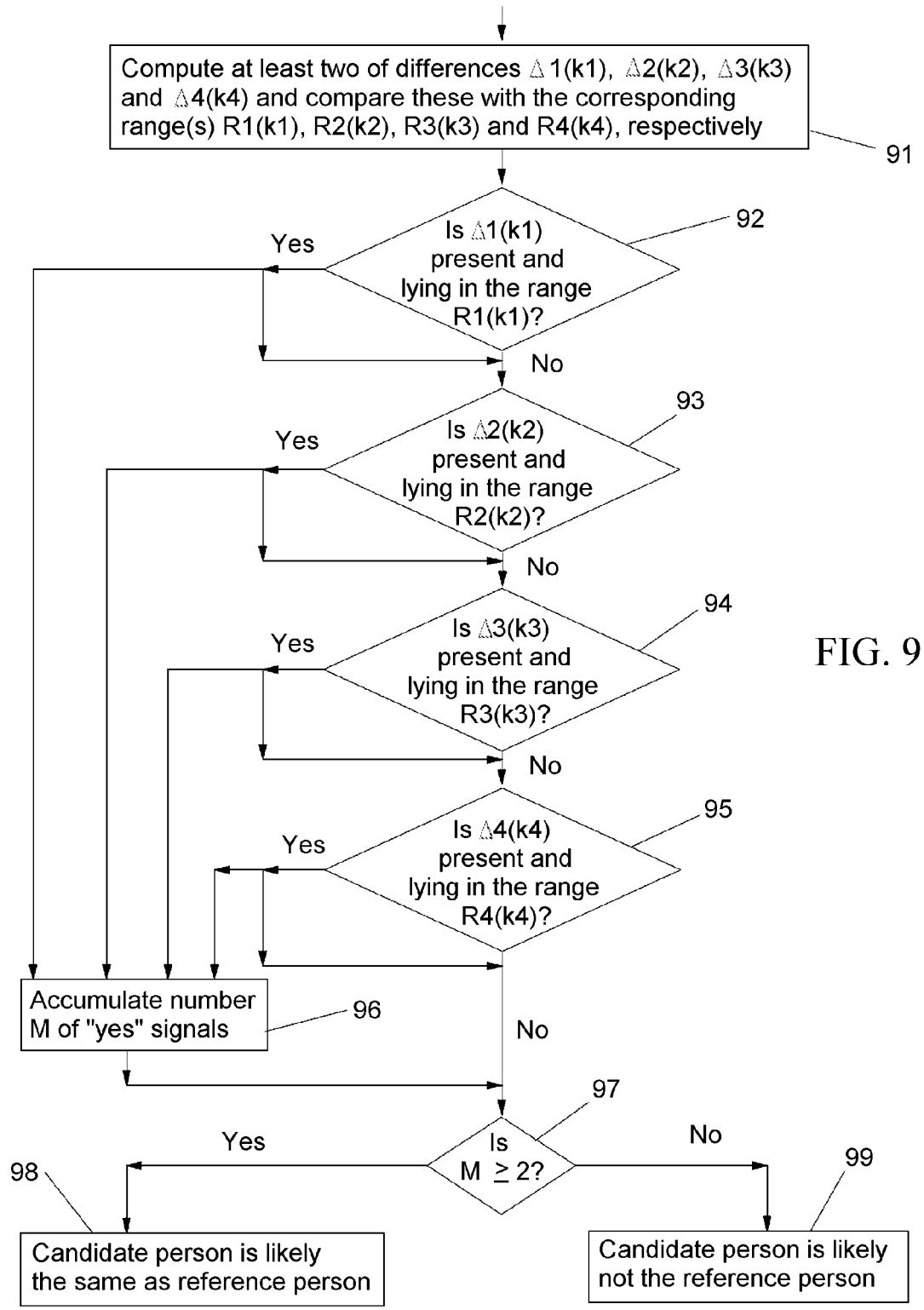

FIG. 9 is a flow chart illustrating a second embodiment of the invention. In step 91, at least two of the difference values, $\Delta 1(k1)$, $\Delta 2(k2)$, $\Delta 3(k3)$ and $\Delta 4(k4)$ are computed and compared with the corresponding ranges, R1(k1), R2(k2), R3(k3) and R4(k4), respectively. The system determines if $\Delta 1(k1)$ is present (computed) and lies in the first range R1(k1), in step 92; if $\Delta 2(k2)$ is present (computed) and lies in the second range R2(k2), in step 93, if $\Delta 3(k3)$ is present (computed) and lies in the third range R3(k3), in step 94, and/or if $\Delta 4(k4)$ is present (computed) and lies in the fourth range R4(k4), in step 95. The number M of "yes" answers in steps 92-95 is accumulated in step 96. If at least two of the answers to the queries in step 92, 93, 94 and 85 is "yes" ($M \geq 2$ in step 97), the system interprets this condition as indicating that the candidate person is likely the reference person, in step 98. If zero or one of the answers to the queries in step 92, step 93, step 94 and step 95 is "yes," the system optionally interprets this condition as indicating that the candidate person is likely not the reference person, in step 99.

Figure 10:
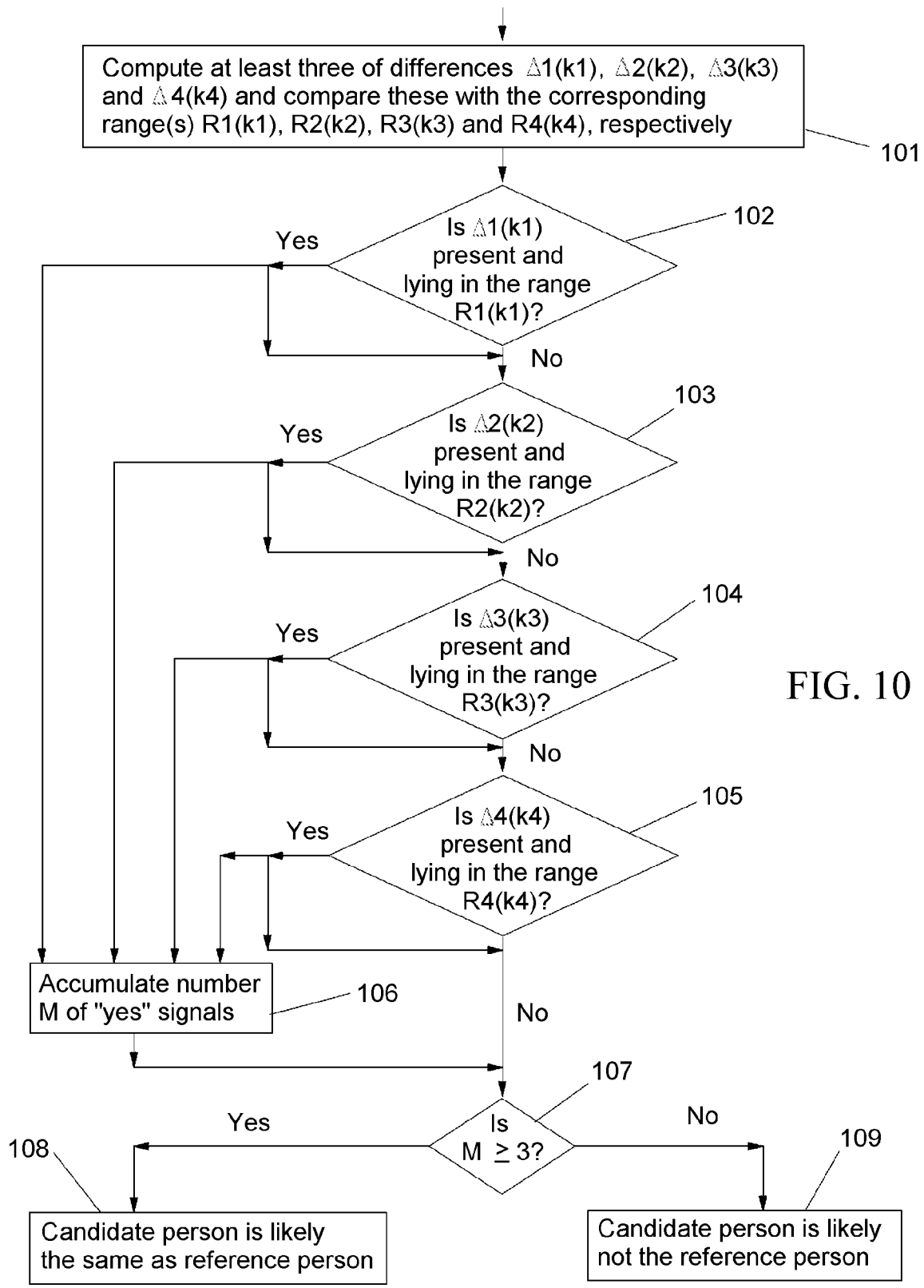

FIG. 10 is a flow chart illustrating a third embodiment of the invention. In step 101, at least three of the difference values, $\Delta 1(k1)$, $\Delta 2(k2)$, $\Delta 3(k3)$ and $\Delta 4(k4)$ are computed and compared with the corresponding ranges, R1(k1), R2(k2), R3(k3) and R4(k4), respectively. The system determines if $\Delta 1(k1)$ is present (computed) and lies in the first range R1(k1), in step 102; if $\Delta 2(k2)$ is present (computed) and lies in the second range R2(k2), in step 103, if $\Delta 3(k3)$ is present (computed) and lies in the third range R3(k3), in step 104, and/or if $\Delta 4(k4)$ is present (computed) and lies in the fourth range R4(k4), in step 105. The number M of "yes" answers in steps 102-105 is accumulated in step 106. If at least three of the answers to the queries in step 102, 103, 104 and 105 is "yes" ($M \geq 3$ in step 107), the system interprets this condition as indicating that the candidate person is likely the reference person, in step 108. If zero, one or two of the answers to the queries in step 102, step 103, step 104 and step 105 is "yes," the system optionally interprets this condition as indicating that the candidate person is likely not the reference person, in step 109.

Figure 11:
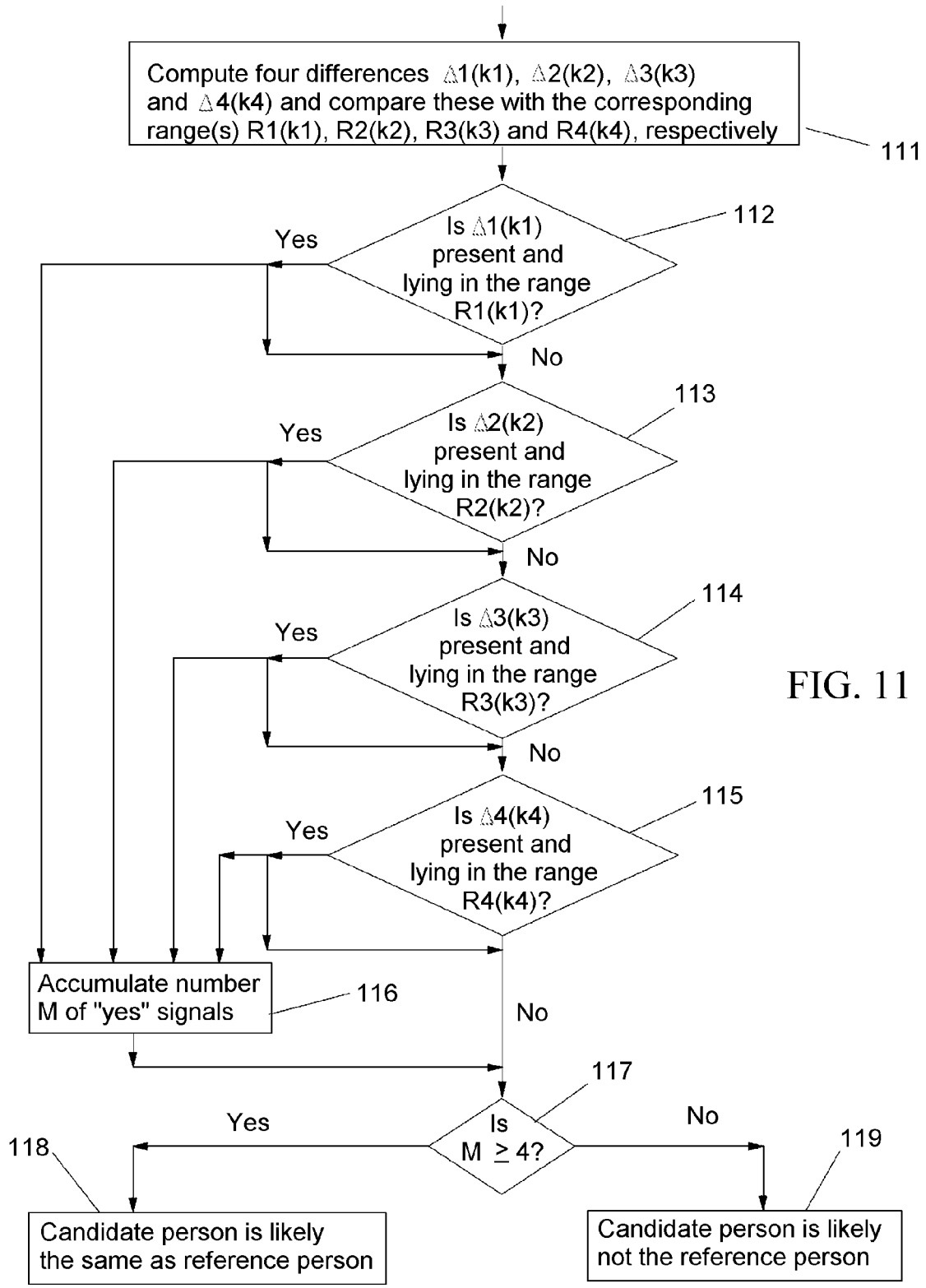
Figure 12:
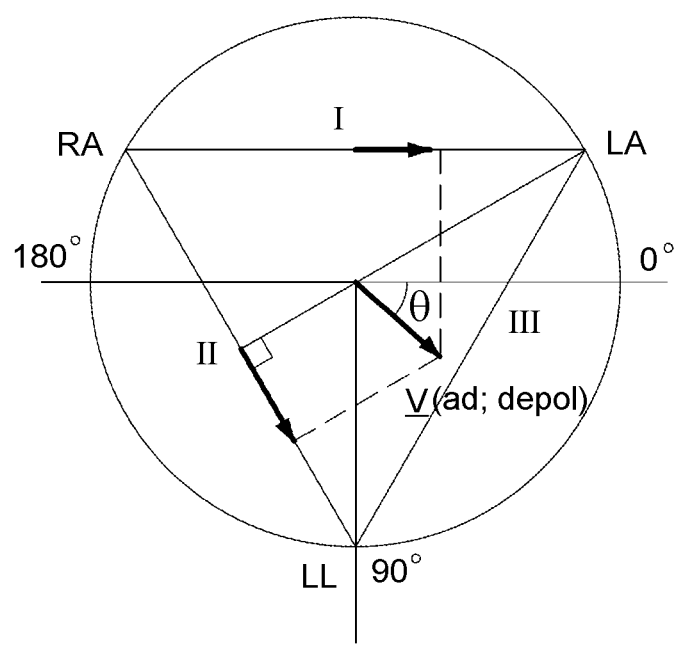
FIG. 12 illustrates the depolarization and repolarization vectors, V(mode;ad;depol), V(mode;vd;depol) and V(mode;vr;repol) associated with a PQRST complex.

FIG. 11 is a flow chart illustrating a fourth embodiment of the invention. In step 111, at least one of each of the four difference values, $\Delta 1(k1)$, $\Delta 2(k2)$, $\Delta 3(k3)$ and $\Delta 4(k4)$ is computed and compared with the corresponding ranges, R1(k1), R2(k2), R3(k3) and R4(k4), respectively. The system determines if $\Delta 1(k1)$ is present (computed) and lies in the first range R1(k1), in step 112; if $\Delta 2(k2)$ is present (computed) and lies in the second range R2(k2), in step 113, if $\Delta 3(k3)$ is present (computed) and lies in the third range R3(k3), in step 114, and/or if $\Delta 4(k4)$ is present (computed) and lies in the fourth range R4(k4), in step 115. The number M of "yes" answers in steps 112-115 is accumulated in step 116. If each of the answers to the queries in step 112, 113, 114 and 115 is "yes" ($M \geq 4$ in step 117), the system interprets this condition as indicating that the candidate person is likely the reference person, in step 118. If fewer than four of the answers to the queries in step 112, step 113, step 114 and step 115 is "yes," the system optionally interprets this condition as indicating that the candidate person is likely not the reference person, in step 119.

Comparison of each of, or a subgroup of, the 15 combinations, sp1(a;meas), sp2(Δt;meas), sp3(θ;meas) and sp4(L; meas), with the corresponding combinations, sp1(a;ref), sp2 (Δt;ref), sp3(θ;ref) and sp4(L;ref), allows discrimination between a candidate person and each of a large number of reference persons. For example, if each of the 15 reference combinations, sp1(a;ref), sp2(Δt;ref), sp3(θ;ref) and sp4(L; ref), has six discrete or distinguishable values, the number of different combinations is $6^{15}$, or about 470 billion. Supplementing these reference measures with the reference cross correlations and cross deviations, <x1·x2;ref>, <Δt1·Δt2; ref>, <θ1·θ3;ref>, <L1·L2;ref>, <x1·Δt2;ref>, <x1·θ3;ref>, <x1·L4;ref>, <Δt1·θ3;ref>, <Δt2·L4> and <θ3·L4;ref> increases the number of combinations by many orders of magnitude so that in principle each person in a population much larger than $1.2 \times 10^{12}$ can be distinguished, using these measures.

Where a reference person is known to have a cardiac-related anomaly or malady that is not transitory (doesn't disappear or sharply diminish with passage of time), and this artifact is manifested by a particular pattern in the PQRST complex, absence of this particular pattern in a PQRST complex presented by a candidate person supports a conclusion that the candidate person is not the reference person, irrespective of agreement or disagreement of other measured statistical parameter values and corresponding reference values. A similar conclusion may be drawn, but is not required, where the candidate person has a non-transitory, cardiac-related anomaly or malady and the reference person does not have the corresponding anomaly or malady.

For example: Δt(p-r;ref)>>200 msec is associated with atrio-ventricular block; Δt(p-r;ref)<120 msec is associated with hypertension and/or paroxysms of tachycardia; Δt(q-s; ref)>120 msec is associated with ventricular arrhythmia or a block of one of the bundles; and presence of a sharply pointed or grossly notched t segment is associated with myocardial infarction (pointed segment) or with pericarditis (notched segment).

The converse is not necessarily true: presence of a particular pattern (anomaly or malady) in a statistical measure, but not in the corresponding pattern for a reference person may support, but does not necessarily require, a conclusion that the candidate person is not the reference person. The reference person may have developed this pattern after the most recent reference pattern was formed.

The ten independent parameters, ap, aq, ar, as, at, Δt(p-q), Δt(q-r), Δt(r-s), Δt(s-t) and Δt(t-p), discussed in the preceding belong to a set of about 192 heart signal parameters, not all of which may be independent. This includes, for example, a post-t plateau region, having an amplitude denoted as a(t; post) (FIG. 2). Ideally, the value of a(t;post) is 0 mV. Where a(t;post)≦−0.5 mV, this condition indicates that the subject has recently experienced a myocardial infarction, probably within the preceding two weeks. Where a(t;post)≦−0.5 mV at a given time, the magnitude |a(t;post)| will decrease with passage of time so that evidence of an earlier myocardial infarction will slowly disappear. An amplitude a(t;post) with a substantial non-zero magnitude, e.g., |a(t;post)|≧0.5 mV, will appear graphically on a only if the frequency range for signal processing extends down to about 0.05 Hz, or lower. Where the frequency range does not extend below about 1 Hz, for example, the amplitude a(t;post) will often have a substantially zero magnitude.

Three other heart signal parameters of interest are the direction of a vector V(mode;ad;depol) for sino atrial-to-atrial-ventricular depolarization, associated with the p segment, the direction of a vector V(mode;vd;depol) for sino atrial-to-atrial-ventricular depolarization, associated with the qrs segment, and the direction of a vector V(mode;vr;repol) for atrial-ventricular repolarization, associated with the t segment, which are expressed as angles θ(mode;ad;depol), θ(mode;vd;depol) and θ(mode;vr;repol), respectively, relative to a horizontal baseline for the subject, as illustrated in FIG. 2. For a given subject, θ(mode;ad;depol), θ(mode;vd; depol) and θ(mode;vr;repol) will have values in ranges of 0°-90°, and these angles do not vary significantly from one heart cycle to the next, absent a deleterious change in the cardio condition of the subject. The angles θ(mode;ad;depol), θ(mode;vd;depol) and θ(mode;vr;repol) for a given subject appear to be independent of each other and can be measured to within an inaccuracy of a few degrees. Thus, for example, an angular range of 0°≦θ≦90° can be decomposed into 6 central angle values, spaced about 15° apart. At least six length values (magnitudes) for each of the corresponding vectors, V(ad;depol), V(vd;depol) and V(vr;repol), are estimated to be distinguishable so that angle and length measurements provide at least 36 distinguishable value pairs.

Figure 13A:
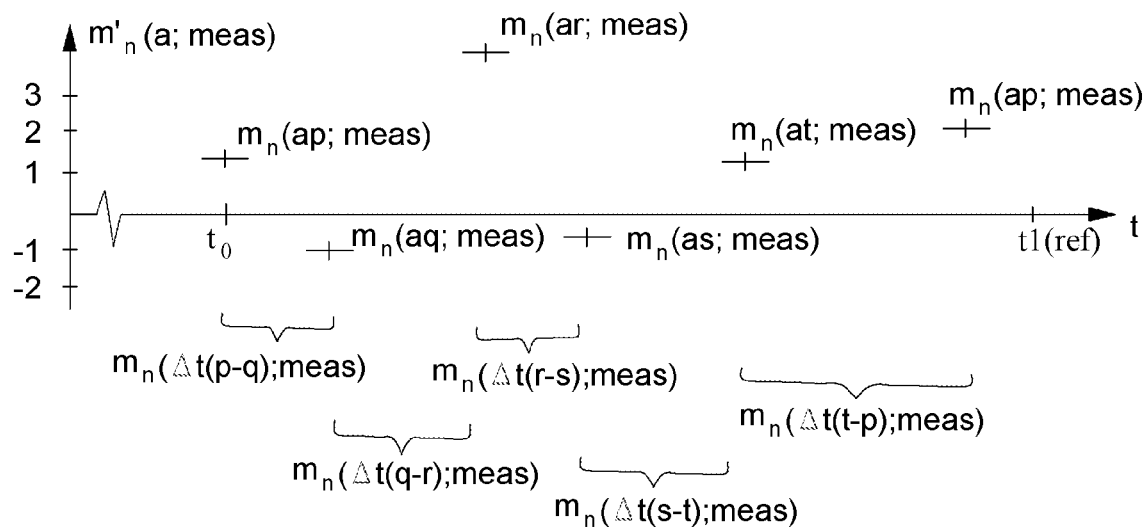
FIGS. 13A, 13B and 13C graphically illustrate a method for displaying and comparing the measured and reference parameter values.
Figure 13B:
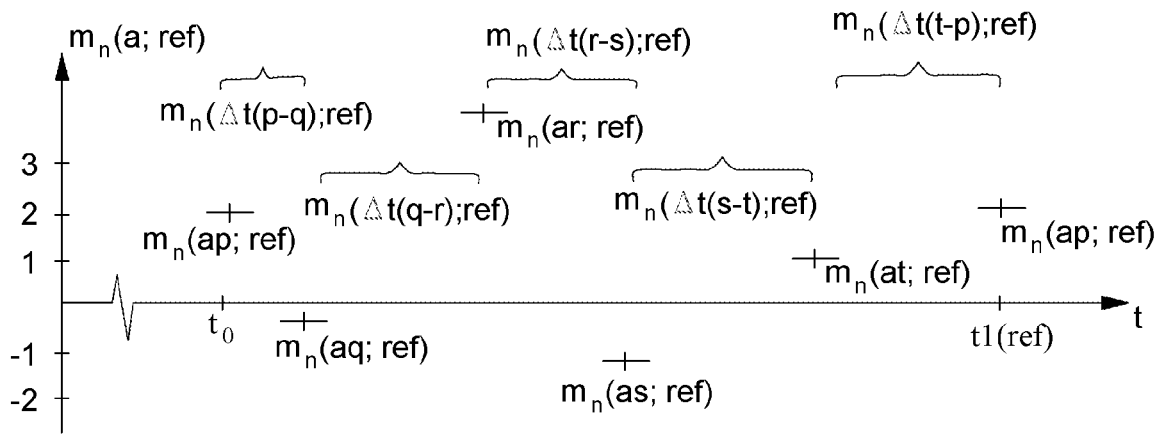

This last number (36), multiplied by an estimated number of independent multi-values of the set {ap, aq, ar, as, at, Δt(p-q), Δt(q-r), Δt(r-s), Δt(s-t), Δt(t-p)} provides a population of about $4.7 \times 10^{11}$ multi-valued sets and associated test subjects that can be discriminated. This number can be further increased by consideration of the cross-correlation values {(ap,aq), (ap,ar), (ap,as), (ap,at), (aq,ar), (aq,as), (aq,at), (ar, as), (ar,at), (as,at), (Δt(p-q),Δt(q-r)), (Δt(p-q),Δt(r-s)), (Δt(p-q),Δt(s-t)), (Δt(q-r),Δt(r-s)), (Δt(q-r),Δt(s-t)), (Δt(r-s),Δt(s-t)), (ap,Δt(p-q), (aq,Δt(p-q), (aq,Δt(q-r), (ar,Δt(q-r), (ar,Δt(r-s), (as,Δt(r-s), (as,Δt(s-t) or (at,Δt(s-t)} discussed in the preceding, so that the total number of test subjects that can be discriminated is estimated to be at least $1.2 \times 10^{12}$.

Where the (normalized) mean value is used for comparison of candidate person parameters versus reference parameters, the ten statistically determined parameters in the set {ap, aq, ar, as, at, Δt(p-q), Δt(q-r), Δt(r-s), Δt(s-t), Δt(t-p)} can be compared in a visually perceptive display as illustrated in FIGS. 13A and 13B. In the xy-graphs in FIG. 13A, the mean peak amplitude values (y-axis, with the associated signums±), $m_n$(ap;meas) vs. $m_n$(ap;ref), $m_n$(aq;meas) vs. $m_n$(aq;ref), $m_n$(ar;meas) vs. $m_n$(ar;ref), $m_n$(as;meas) vs. $m_n$(as;ref), $m_n$(at;meas) vs. $m_n$(at;ref), and $m_n$(ap;meas) vs. $m_n$(ap;ref), are compared, in pairs, by vertical separation of horizontal line segments, one above the other for each pair. These pairs of peak amplitude values can be compared with reference to the respective y-axis values, $m_n$(a;meas) and $m_n$(a;ref) in FIG. 13A.

The x-axes, representing time, in FIG. 13A are aligned with the same initial value, t=t0(ref)=t0(meas), representing the times of the respective peak amplitudes for the P-wave, a=ap, and a final time value, t=t1(ref) or t=t1(meas), representing the next succeeding time value for beginning of a new PQRST cycle for the reference complex; the value t=t1(ref) may not coincide with a corresponding time value, t=t1 (meas) for the measured PQRST complex.

A center point, corresponding to peak amplitude, for each horizontal segment in the sequence {$m_n$(ap;meas), $m_n$(aq; meas), $m_n$(ar;meas). $m_n$(as;meas), $m_n$(at;meas), $m_n$(ap; meas)} is separated in time (x-axis) from the next succeeding horizontal segment by a temporal distance $m_n$(Δt;meas), with Δt=Δt(p-q), Δt(q-r), Δt(r-s), Δt(s-t) and Δt(t-p), in FIG. 13A In a similar manner, a center point, corresponding to peak amplitude, for each horizontal segment in the sequence {$m_n$(ap; ref), $m_n$(aq;ref), $m_n$(ar;ref). $m_n$(as;ref), $m_n$(at;ref), $m_n$(ap; ref)} is separated in time (x-axis) from a center point for the next succeeding horizontal segment by a temporal distance $m_n(\Delta t;\text{ref})$. The pairs of peak amplitude time intervals, $m_n(\Delta t(p-q))$ and $m_n(\Delta t(p-q);\text{ref})$, $m_n(\Delta t(q-r))$ and $m_n(\Delta t(q-r);\text{ref})$, $m_n(\Delta t(r-s))$ and $m_n(\Delta t(r-s);\text{ref})$, $m_n(\Delta t(s-t))$ and $m_n(\Delta t(s-t);\text{ref})$, and $m_n(\Delta t(t-p);\text{meas})$ and $m_n(\Delta t(t-p);\text{ref})$, can be compared with reference to the respective x-axis values, $m_n(\Delta t);\text{meas})$ 13A and $m_n(\Delta t;\text{ref})$ in FIG. 13A). Display of these mean value pairs on the same graph may allow easier comparison of the corresponding mean values. The mean values, $m_n(a;\text{meas})$ and $m_n(a;\text{ref})$, can be replaced by the corresponding standard deviation values, $sd_n(a;\text{meas})$ and $sd_n(a;\text{ref})$, in FIG. 13A, if desired.

Figure 13C:
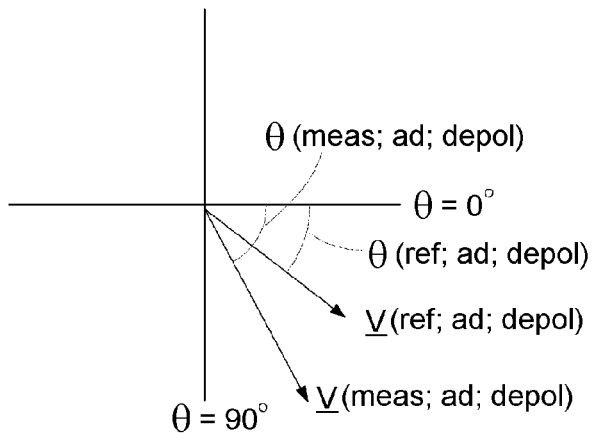
Figure 13D:
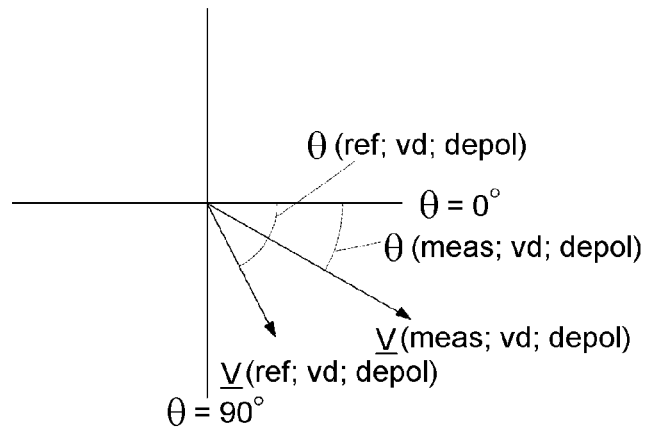
Figure 13E:
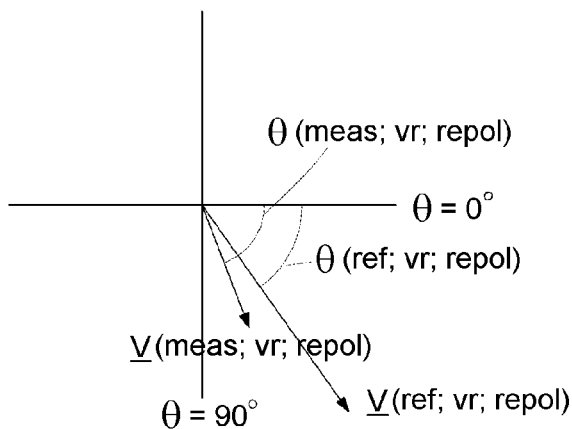

FIGS. 13C-13E graphically compares the mean values, $m_n(\theta;\text{mode};\text{meas})$ and $m_n(\theta;\text{mode};\text{ref})$, for the waves associated with the atrial depolarization vectors $V(\theta;ad;\text{meas})$ and $V(\theta;ad;\text{ref})$, for the waves associated with the ventricular depolarization vectors $V(\theta;vd;\text{meas})$ and $V(\theta;vd;\text{ref})$, and for the waves associated with the ventricular repolarization vectors. $V(\theta;vr;\text{meas})$ and $V(\theta;vr;\text{ref})$, where each depolarization and repolarization vector V can be represented by an angle $\theta$ relative to an x-axis ($\theta=0°$) and a length $L=|V|$ representing intensity of the vector V. The mean values, $m_n(\theta;\text{mode};\text{meas})$, $m_n(\theta;\text{mode};\text{ref})$, $m_n(L;\text{mode};\text{meas})$ and $m_n(L;\text{mode};\text{ref})$, can be replaced by the corresponding standard deviation values, $sd_n(\theta;\text{mode};\text{meas})$, $sd_n(\theta;\text{mode};\text{ref})$, $sd_n(L;\text{mode};\text{meas})$ and $sd_n(L;\text{mode};\text{ref})$, in FIGS. 13C-13E, if desired. In each instance, the "measured" value is a statistical value, measured over many heart cycles for the candidate person whose asserted identity is to be confirmed or refuted.

Full application of the ECG analysis discussed here is, admittedly, fairly complex, although the richness and diversity of the results are often an ample reward for the effort. The analysis, results and conclusions discussed here can be applied wherever access to a facility or to selected information is limited to a small number of certified individuals. The applications include: access to information and/or to modification of information in banking and money handling/transfer activities; access to weapons storage and weapons maintenance facilities; access to encryption codes and associated keys; and authentication (or refutation of) an identity asserted by a candidate person in a relatively short time interval (a few minutes). It may be possible, for some purposes, to replace this full ECG analysis with a modified version in which, as one example, timed measurements of signals sensed at two or more fingers or thumbs, pressed against separate sensing pads, and time shifted correlations are analyzed to distinguish between certain persons. activities; access to weapons storage and weapons maintenance facilities; access to encryption codes and associated keys; and authentication (or refutation of) an identity asserted by a candidate person in a relatively short time interval (a few minutes). It may be possible, for some purposes, to replace this full ECG analysis with a modified version in which, as one example, timed measurements of signals sensed at two or more fingers or thumbs, pressed against separate sensing pads, and time shifted correlations are analyzed to distinguish between certain persons.

Sensor placement, for purposes of reading signals that result in the PQRST complex may be constrained by religious or cultural values that limit or prohibit contact of any device with the human body. Where this occurs and comparison of the PQRST complexes is central to identity authentication, the candidate person may have to be denied access to whatever site or object or information that person seeks.

APPENDIX

Application of Maximum Likelihood Classification to Parameters

The asserted identity of a candidate person can be verified or refuted using a subset, or the full set, of the features discussed in the preceding, but employing a statistical classification method based on a Gaussian Mixture Model (GMM). The features, preferably in dimensionless format, can be concatenated into a feature vector x of dimension D. Data from a particular ECG training set (reference person) are collected to construct a statistical model, referred to as a GMM. For verification purposes, new data are scored against the GMM that corresponds to the asserted identity.

The verification uses a likelihood function, based on N mixture components, $$\rho(x|M) = \Sigma_i w_i \rho_i(x), \qquad (A\text{-}1)$$

applied to a test feature vector x for the model M, where $\rho_i(x)$ is an ith mixture, modeled as a Gaussian density function, and $w_i$ is a non-negative weight value associated with the mixture number i and satisfying $$\Sigma_i w_i = 1. \qquad (A\text{-}2)$$

Each density function is assumed to have a Gaussian form, $$\rho_i(x;\rho_i) = \{(2\pi)^{D/2} \|C_i\|^{1/2}\}^{-1} \exp\{-(x-\mu_i^{tr}(C_i^{-1})(x-\mu_i)/2\}, \qquad (A\text{-}3)$$

where $\mu_i$ is a vector mean, determined from the training data and $C_i$ is a covariance matrix for the ith Gaussian mixture density for the model M, both determined from the training data (reference person), and x is a corresponding feature vector determined from the test data (candidate person). Training data are multiple feature vectors $x_j$ recorded for the reference person at various times before testing of the candidate person.

The overall density function is assumed to be a product of the density functions $\rho_j(X_j|M)$ corresponding to the jth vector density. A logarithm of the likelihood function $$L = \log\{\rho(X|M)\} = \Sigma_j \log \rho(X_j|M) \qquad (A\text{-}4)$$

is used here as a discriminat function, where X is a global vector referring to the collection of vectors $\{x_j\}_j$, and L is partially differentiated with respect to each of the vector parameters components $\mu_i$ to estimate optimum parameter values and any other parameters of interest. The solution parameters are substituted in the expression for $\rho_i$ in Eq. (A-3), together with measured values for the test vector x, and the density function numerical value (DFNV) is compared with a selected threshold value. If DFNV is at least equal to the threshold value, this condition is interpreted as indicating that the candidate person is likely the same as the reference person. If DFNV is less than the threshold value, this condition may be interpreted as indicating that the candidate person is likely not the reference person. The MLE procedure is discussed in Jae Myung, "Tutorial on maximum likelihood estimation," Jour. Of Math. Psychology, vol. 47 (2003), pp. 90-100, incorporated by reference herein. The MLE approach requires considerable effort to gather sufficient training data but has the advantage that use of an extraneous error metric, such as the Minkowski distance(s) in Eqs. (17)-(20), need not be imposed.

Where optimal values of the vector means $\mu_i$ have been determined, using the procedure indicated above, the measured vector values, or a mean value of the vector values x, can be inserted into Eq. (A-3), using the optimal values of the vector means $\mu_i$, and a numerical value for the density function $\rho(x;\mu_i)$ can be computed. If this numerical value lies in a selected numerical range, this condition is interpreted as indicating that the andidate person is likely to be the reference person. If this numerical value does not lie in the selected numerical range, this condition is optionally interpreted as indicating that the andidate person is likely not the reference person.

What is claimed is:

1. A method for estimating an identity of a candidate person, the method comprising:

providing a sequence of measured values of at least one time interval length value, drawn from a set of measured time interval length values, $\Delta t = \Delta t(p-q)$, $\Delta t = \Delta t(q-r)$, $\Delta t = \Delta t(r-s)$, $\Delta t = \Delta t(s-t)$ and $\Delta t = \Delta t(t-p)$, corresponding to a P wave, a Q wave, an R wave, an S wave and a T wave, respectively, for a sequence of PQRST electrical signal heart complexes for a candidate person;

computing at least one measured statistical parameter, drawn from a set of parameters sp2($\Delta t$;meas), comprising normalized mean $m_n(\Delta t;meas)$, normalized standard deviation $sd_n(\Delta t;meas)$, skewness $sk(\Delta t;meas)$ and kurtosis $ku(\Delta t;meas)$, for the at least one measured time interval length, $\Delta t = \Delta t(p-q)$, $\Delta t = \Delta t(q-r)$, $\Delta t = \Delta t(r-s)$, $\Delta t = \Delta t(s-t)$ and $\Delta t = \Delta t(t-p)$, for the sequence of PQRST complexes associated with the candidate person;

providing at least one reference statistical parameter, drawn from a set sp2($\Delta t$;ref), of reference parameters comprising normalized mean $m_n(\Delta t;ref)$, normalized standard deviation $sd_n(\Delta t;ref)$, skewness $sk(\Delta t;ref)$ and kurtosis $ku(\Delta t;ref)$, for at least one reference time interval length, $\Delta t = \Delta t(p-q)$, $\Delta t = \Delta t(q-r)$, $\Delta t = \Delta t(r-s)$, $\Delta t = \Delta t(s-t)$ and $\Delta t = \Delta t(t-p)$, for PQRST complexes associated with a known reference person;

forming a difference, $\Delta 2(k2)$, numbered $k2=1, \ldots, K2$ ($K2 \geq 1$), dependent upon a magnitude of at least one of the differences, $m_n(\Delta t;meas) - m_n(\Delta t;ref)$, $sd_n(\Delta t;meas) - sd_n(\Delta t;ref)$, $sk(\Delta t;meas) - sk(\Delta t;ref)$, and $ku(\Delta t;meas) - ku(\Delta t;ref)$, of statistical parameters drawn from the sets sp2($\Delta t$;meas) and sp2($\Delta t$;ref), multiplied by a non-negative weight value, w1', w2', w3' and w4', respectively;

when $\Delta 2(k2)$ lies in a selected range R2(k2) of values, interpreting satisfaction of this condition as indicating that the candidate person is likely to be the reference person; and when $\Delta 2(k2)$ does not lie in the range R2(k2) of values, interpreting non-satisfaction of this condition as indicating that the candidate person is not likely to be the reference person;

displaying or otherwise indicating at least one of (i) the interpretation that the candidate person is likely to be the reference person and (ii) the interpretation that the candidate person is not likely to be the reference person.

2. The method of claim 1, further comprising choosing said difference $\Delta 2(k2)$ to comprise $$\Delta 2(k2) = \{w1'|m_1(\Delta t;meas) - m_n(\Delta t;ref)|^{f2} + w2'|sd_n(\Delta t;meas) - sd_n(\Delta t;ref)|^{f2} + w3'|sk(\Delta t;meas) - sk(\Delta t;ref)|^{f2} + w4'|ku(\Delta t;meas) - ku(\Delta t;ref)|^{f2}\}^{1/f2},$$

where f2 is a selected positive number.

3. The method of claim 1, further comprising:
providing, as said reference person, a person who has an abnormal feature, associated with a medical condition that is not transitory, and associated with at least one of said at least one reference statistical parameters, for at least one of said time interval length values, $\Delta t = \Delta t(p-q)$, $\Delta t = \Delta t(q-r)$, $\Delta t = \Delta t(r-s)$, $\Delta t = \Delta t(s-t)$ and $\Delta t = \Delta t(t-p)$; and when said candidate person has a measured statistical parameter, for said corresponding time interval length value $\Delta t$ that does not include the abnormal feature, interpreting this condition as indicating that said candidate person is likely not said reference person.

4. The method of claim 1, further comprising:
providing, as said reference person, a person who does not have an abnormal feature, associated with a medical condition that is not transitory, associated with at least one of said at least one reference statistical parameters, for at least one of said time interval length values, $\Delta t = \Delta t(p-q)$, $\Delta t = \Delta t(q-r)$, $\Delta t = \Delta t(r-s)$, $\Delta t = \Delta t(s-t)$ and $\Delta t = \Delta t(t-p)$, and when said candidate person has a measured statistical parameter, for said corresponding time interval length value $\Delta t$ that does include the abnormal feature, interpreting this condition as indicating that said candidate person is likely not said reference person.

5. The method of claim 1, further comprising:
displaying, at least one of said measured statistical parameter values, normalized mean $m_n(\Delta t;meas)$, normalized standard deviation $sd_n(\Delta t;meas)$, skewness $sk(\Delta t;meas)$ and kurtosis $ku(\Delta t;meas)$; and displaying at least one of said reference statistical parameter values, normalized mean $m_n(\Delta t;ref)$, normalized standard deviation $sd_n(\Delta t;ref)$, skewness $sk(\Delta t;ref)$ and kurtosis $ku(\Delta t;ref)$ corresponding to the at least one of said measured statistical parameter values.

6. The method of claim 5, further comprising displaying said at least one of said measured statistical parameter values, and said least one of said corresponding reference parameter values, on a first xy-graph.

7. The method of claim 6, wherein:
said at least one measured statistical parameter value is displayed on said first graph as a line segment, substantially parallel to an x-axis of said first graph with a first y-value on a y-axis of said first graph corresponding to said at least one measured statistical parameter value; and said at least one corresponding reference statistical parameter value is displayed on said first graph as a line segment substantially parallel to the x-axis on said graph, with a second y-value on the y-axis of said first graph corresponding to said at least one corresponding reference statistical parameter value, where the x-axis of said first graph represents time for said measured statistical parameter values, $\Delta t = \Delta t(p-q)$, $\Delta t = \Delta t(q-r)$, $\Delta t = \Delta t(r-s)$, $\Delta t = \Delta t(s-t)$ and $\Delta t = \Delta t(t-p)$, and represents time for said reference statistical parameter values, $\Delta t = \Delta t(p-q)$, $\Delta t = \Delta t(q-r)$, $\Delta t = \Delta t(r-s)$, $\Delta t = \Delta t(s-t)$ and $\Delta t = \Delta t(t-p)$.

8. The method of claim 5, further comprising displaying said at least one measured statistical parameter value, on a first xy-graph, and displaying said at least one corresponding reference parameter value on a second xy-graph.

9. The method of claim 6, further comprising:
displaying said at least one measured statistical parameter value on said first graph as a line segment substantially parallel to an x-axis on said first graph, with a first y-value on a y-axis of said first graph corresponding to said at least one measured statistical parameter value; and displaying said at least one corresponding reference statistical parameter value on a second graph as a line segment substantially parallel to an x-axis on said second graph, with a y-value on a y-axis of the second graph corresponding to said at least one reference statistical parameter value, where an x-axis of said first graph, representing time, and an x-axis of the second graph, representing time, are aligned with reference to (i) a time of occurrence of said measured time interval length value, $\Delta t = \Delta t(p-q)$, $\Delta t = \Delta t(q-r)$, $\Delta t = \Delta t(r-s)$, $\Delta t = \Delta t(s-t)$ and $\Delta t = \Delta t(t-p)$, for said measured statistical parameter values and (ii) a time of occurrence of said corresponding reference peak amplitude value, $\Delta t=\Delta t(p-q)$, $\Delta t=\Delta t(q-r)$, $\Delta t=\Delta t(r-s)$, $\Delta t=\Delta t(s-t)$ and $\Delta t=\Delta t(t-p)$, for said reference statistical parameter values.

* * * * *